(12) United States Patent
Li et al.

(10) Patent No.: US 11,432,737 B2
(45) Date of Patent: Sep. 6, 2022

(54) SYSTEMS AND METHODS FOR REAL-TIME MOTION PREDICTION IN DYNAMIC IMAGING

(71) Applicant: The Regents of the University of California, Oakland, CA (US)

(72) Inventors: Xinzhou Li, Los Angeles, CA (US); Holden H. Wu, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 226 days.

(21) Appl. No.: 16/492,295

(22) PCT Filed: Mar. 17, 2018

(86) PCT No.: PCT/US2018/023037
§ 371 (c)(1),
(2) Date: Sep. 9, 2019

(87) PCT Pub. No.: WO2018/170499
PCT Pub. Date: Sep. 20, 2018

(65) Prior Publication Data
US 2020/0008707 A1    Jan. 9, 2020

Related U.S. Application Data

(60) Provisional application No. 62/473,286, filed on Mar. 17, 2017.

(51) Int. Cl.
*A61B 5/055* (2006.01)
*G06T 7/11* (2017.01)
(Continued)

(52) U.S. Cl.
CPC .............. *A61B 5/055* (2013.01); *A61B 5/725* (2013.01); *A61B 6/032* (2013.01); *A61B 8/5276* (2013.01);
(Continued)

(58) Field of Classification Search
CPC ......... A61B 5/055; A61B 5/725; A61B 6/032; A61B 8/5276; A61B 5/7207;
(Continued)

(56) References Cited

U.S. PATENT DOCUMENTS 7,907,987 B2    3/2011  Dempsey
2007/0253599 A1 * 11/2007  White .............. G01R 33/56509
                                                              382/107
(Continued)

FOREIGN PATENT DOCUMENTS

| KR | 20170017156 A | * | 2/2017 | ............... A61B 6/00 |
| KR | 20170017156 A | | 2/2017 | |
| WO | 2015161059 A1 | | 10/2015 | |

OTHER PUBLICATIONS

Seo et al. 2001 Proc. IEEE CVPR 2001 I-1148-I-1154 (Year: 2003).*

(Continued)

*Primary Examiner* — Colin T. Sakamoto
*Assistant Examiner* — Patrick M Mehl
(74) *Attorney, Agent, or Firm* — Quarles & Brady LLP

(57) ABSTRACT

Systems and methods for predicting motion of a target using imaging are provided. In one aspect, a method includes receiving image data, acquired using an imaging system, corresponding to a region of interest ("ROI") in a subject, and generating a set of reconstructed images from the image data. The method also includes processing the set of reconstructed images to obtain motion information associated with a target in the ROI, and applying the motion information in a motion prediction framework to estimate a predicted motion of the target. The method further includes generating a report based on the predicted motion estimated.

16 Claims, 17 Drawing Sheets

(51) Int. Cl.
  *G06T 7/277* (2017.01)
  *A61B 5/00* (2006.01)
  *A61B 6/03* (2006.01)
  *G06T 7/00* (2017.01)
  *A61B 8/08* (2006.01)
(52) U.S. Cl.
  CPC .............. *G06T 7/0016* (2013.01); *G06T 7/11* (2017.01); *G06T 7/277* (2017.01); *G06T 2207/10088* (2013.01); *G06T 2207/20104* (2013.01)
(58) Field of Classification Search
  CPC ..... A61B 2576/00; A61B 6/5264; A61B 5/11; A61B 6/037; G06T 7/0016; G06T 7/11; G06T 7/277; G06T 2207/10088; G06T 2207/20104; G06T 2207/30004; G16H 30/40; G01R 33/56509; G01R 33/5608
  See application file for complete search history.

(56) References Cited

U.S. PATENT DOCUMENTS

| | | | |
|---|---|---|---|
| 2010/0183206 A1 | 7/2010 | Carlsen | |
| 2011/0144495 A1* | 6/2011 | Wilkening | A61B 8/483 600/443 |
| 2016/0073962 A1* | 3/2016 | Yu | A61B 5/1127 600/407 |
| 2016/0310082 A1 | 10/2016 | Rajamani | |
| 2017/0078575 A1 | 3/2017 | Ryu | |

OTHER PUBLICATIONS

Riu et al. 2013 Proc. SPIE 8897 11 pages (Year: 2013).*
Stoianovici et al. 2007 Minim. Invasive Ther. Allied Technol. 16:241-248 (Year: 2007).*
Adelson, E. H., et al. "Pyramid methods in image processing." RCA engineer 29.6 (1984): 33-41.
Adluru, G., et al. "Acquisition and reconstruction of undersampled radial data for myocardial perfusion magnetic resonance imaging." Journal of Magnetic Resonance Imaging: An Official Journal of the International Society for Magnetic Resonance in Medicine 29.2 (2009): 466-473.
Alexander, HL. State Estimation for Distributed Systems with Sensing Delay. In: SPIE , Orlando, 1991;Data Structures and Target Classification 1470:103-111.
Arai, TJ, et al. "Characterizing spatiotemporal information loss in sparse-sampling-based dynamic MRI for monitoring respiration-induced tumor motion in radiotherapy." Medical physics 43.6Part1 (2016): 2807-2820.
Bernstein, M. A., et al. "Effect of windowing and zero-filled reconstruction of MRI data on spatial resolution and acquisition strategy." Journal of Magnetic Resonance Imaging: An Official Journal of the International Society for Magnetic Resonance in Medicine 14.3 (2001): 270-280.
Bjerre, T., et al. "Three-dimensional MRI-linac intra-fraction guidance using multiple orthogonal cine-MRI planes." Physics in Medicine & Biology 58.14 (2013): 4943.
Digalakis V., et al., "ML estimation of a stochastic linear system with the EM algorithm and its application to speech recognition," IEEE Trans. Speech Audio Process., vol. 1, No. 4, pp. 431-442, 1993.
Fatehi A et al, "Kalman filtering approach to multi-rate information fusion in the presence of irregular sampling rate and variable measurement delay," J. Process Control, vol. 53, pp. 15-25, 2017.
Ge Y. et al., "Toward the development of intrafraction tumor deformation tracking using a dynamic multi-leaf collimator," Med. Phys., vol. 41, No. 6, 2014.

Gopalakrishnan A, et al. Incorporating delayed and infrequent measurements in Extended Kalman Filter based nonlinear state estimation. J Process Control 2011;21:119-129.
Green OL et al., "First clinical implementation of real-time, real anatomy tracking and radiation beam control," Med. Phys., vol. 45, No. 8, pp. 3728-3740, Aug. 2018.
Hansen MS et al, "Gadgetron: An open source framework for medical image reconstruction," Magn. Reson. Med., vol. 69, No. 6, pp. 1768-1776, 2013.
Ingle RR et al., "Nonrigid autofocus motion correction for coronary MR angiography with a 3D cones trajectory," Magn. Reson. Med., vol. 72, No. 2, pp. 347-361, Aug. 2014.
International Searching Authority, International Search Report and Written Opinion for application PCT/US2018/023037, dated Jun. 15, 2018, 15 pages.
Keall PJ et al., "The management of respiratory motion in radiation oncology report of AAPM Task Group 76a)," Med. Phys., vol. 33, No. 10, pp. 3874-3900, Sep. 2006.
Larsen TD, et al. incorporation of time delayed measurements in a discrete-time Kalman filter. IEEE Conf Decis Control 1998;4:3972-7.
Li, X, et al. Real-Time Motion Prediction for Feedback Control of MRI-Guided Interventions. Proceedings of the ISMRM 25th Annual Meeting, Honolulu, 2017, p. 5540.
Li, X. et al, "Motion prediction using a multi-rate Kalman Filter with golden angle radial acquisition for real-time MRI-guided interventions," Proc. ISMRM 26th Annu. Meet., p. 4151, 2018.
Murphy, K,. Kalman Filter Toolbox For Matlab. 2004. http://www.cs.ubc.ca/~murphyk/Software/Kalman/kalman.html.
Paganelli C, et al, et al. Magnetic resonance imaging-guided versus surrogate-based motion tracking in liver radiation therapy: A prospective comparative study. Int J Radiat Oncol Biol Phys 2015;91:840-848.
Ramrath L, et al. Prediction of respiratory motion with a multi-frequency based extended Kalman filter. In: Proceedings of the 21st international conference and exhibition on computer assisted radiology and surgery (CARS'07), Germany, 2007.
Rasche V. et al., "Continuous radial data acquisition for dynamic MRI," Magn. Reson. Med., vol. 34, No. 5, pp. 754-761, Nov. 1995.
Ries M, et al. Real-time 3D target tracking in MRI guided focused ultrasound ablations in moving tissues. Magn Reson Med 2010;64:1704-12.
Roujol S. et al., "Real-time MR-thermometry and dosimetry for interventional guidance on abdominal organs," Magn. Reson. Med., vol. 63, No. 4, pp. 1080-1087, 2010.
Ruan, D. et al. "Image-guided positioning and tracking." The Cancer Journal 17.3 (2011): 155-158.
Ruan, D. et al. "Real-time prediction of respiratory motion based on local regression methods." Physics in Medicine & Biology 52.23 (2007): 7137.
Ruan, D., et al. "Online prediction of respiratory motion: multidimensional processing with low-dimensional feature learning." Physics in Medicine & Biology 55.11 (2010): 3011.
Seregni M. et al., "A Hybrid image registration and matching framework for real-time motion tracking in MRI-guided radiotherapy," IEEE Trans. Biomed. Eng., vol. 65, No. 1, pp. 131-139, 2018.
Seregni, M., et al. "Motion prediction in MRI-guided radiotherapy based on interleaved orthogonal cine-MRI." Physics in Medicine & Biology 61.2 (2016): 872.
Sharp, GC, et al. "Prediction of respiratory tumour motion for real-time image-guided radiotherapy." Physics in Medicine & Biology 49.3 (2004): 425.
Shi X. et al., "Evaluation of template matching for tumor motion management with cine-MR images in lung cancer patients," Med. Phys., vol. 41, No. 5, 2014.
Sørensen TS et al., "Real-time reconstruction of sensitivity encoded radial magnetic resonance imaging using a graphics processing unit," IEEE Trans. Med. Imaging, vol. 28, No. 12, pp. 1974-1985, 2009.

(56) References Cited

OTHER PUBLICATIONS

Spincemaille, P, et al. "Kalman filtering for real-time navigator processing." Magnetic Resonance in Medicine: An Official Journal of the International Society for Magnetic Resonance in Medicine 60.1 (2008): 158-168.
Stoianovici, D, et al. ""MRI Stealth" robot for prostate interventions." Minimally Invasive Therapy & Allied Technologies 16.4 (2007): 241-248.
Welch G, et al. An introduction to the Kalman filter. In: Proceedings of the Siggraph Course, Los Angeles, 2001.
Winkelmann S, et al. An optimal radial profile order based on the Golden Ratio for time-resolved MRI. IEEE Trans Med Imaging 2007;26:68-76.
Wu, HH, et al. "Free-breathing multiphase whole-heart coronary MR angiography using image-based navigators and three-dimensional cones imaging." Magnetic resonance in medicine 69.4 (2013): 1083-1093.
Zachiu C. et al., "An improved optical flow tracking technique for real-time MR-guided beam therapies in moving organs," Phys. Med. Biol., vol. 60, No. 23, p. 9003, 2015.

\* cited by examiner

FIG. 8A
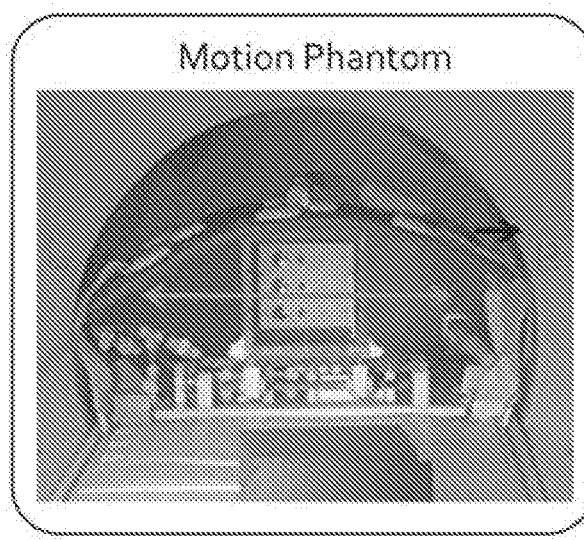
FIG. 8B
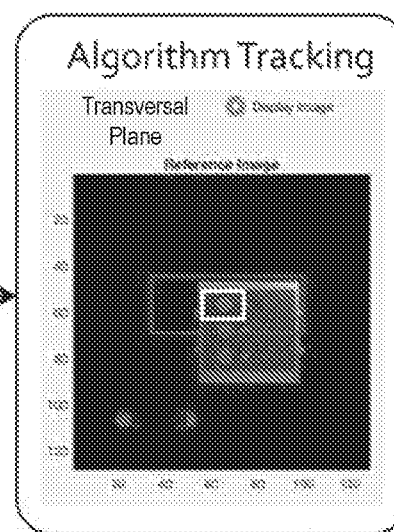
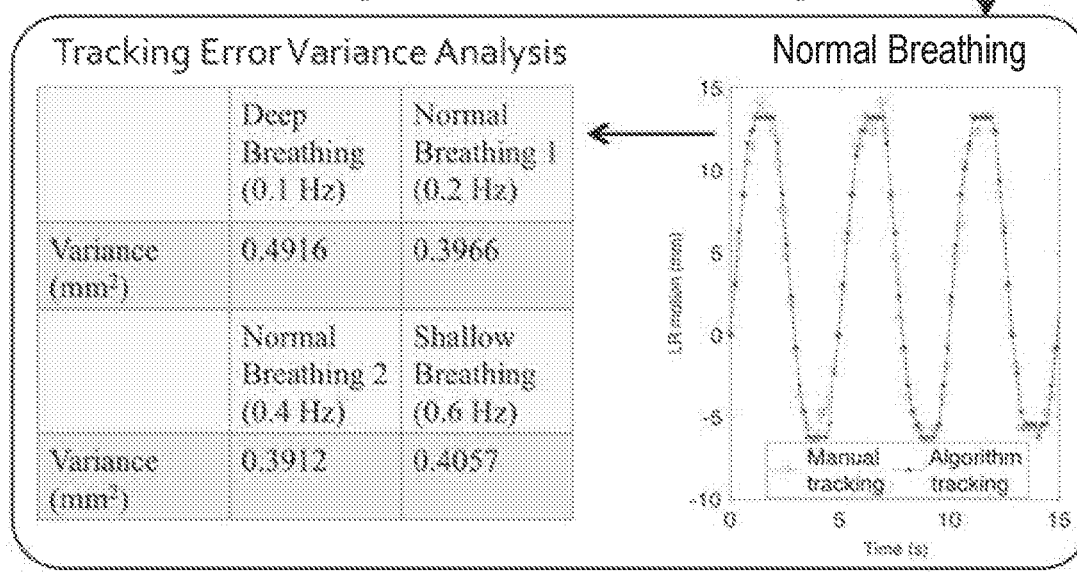
FIG. 8C

SYSTEMS AND METHODS FOR REAL-TIME MOTION PREDICTION IN DYNAMIC IMAGING

CROSS-REFERENCE TO RELATED APPLICATIONS

This application is based on, claims priority to, and incorporates herein by reference in its entirety, U.S. Application 62/473,286 filed on Mar. 17, 2017, and entitled "SYSTEMS AND METHODS FOR REAL-TIME MOTION PREDICTION IN DYNAMIC IMAGING."

BACKGROUND

The present disclosure relates generally to systems and methods for medical imaging and, in particular, to systems and methods for motion prediction in dynamic imaging.

Any nucleus that possesses a magnetic moment attempts to align itself with the direction of the magnetic field in which it is located. In doing so, however, the nucleus precesses around this direction at a characteristic angular frequency (Larmor frequency), which is dependent on the strength of the magnetic field and on the properties of the specific nuclear species (the gyromagnetic ratio $\gamma$ of the nucleus). Nuclei which exhibit these phenomena are referred to herein as "spins."

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a transient radiofrequency electromagnetic pulse (excitation field $B_1$) which is in the x-y plane and which is near the Larmor frequency, the net aligned moment, $M_z$, may be rotated, or "tipped", into the x-y plane to produce a net transverse magnetic moment Mt, which is rotating, or spinning, in the x-y plane at the Larmor frequency. The practical value of this phenomenon resides on signals that are emitted by the excited spins after the pulsed excitation signal $B_1$ is terminated. Depending upon chemically and biologically determined variable parameters such as proton density, longitudinal relaxation time ("T1") describing the recovery of $M_z$ along the polarizing field, and transverse relaxation time ("T2") describing the decay of Mt in the x-y plane, this nuclear magnetic resonance ("NMR") phenomena is exploited to obtain image contrast and concentrations of chemical entities or metabolites using different measurement sequences and by changing imaging parameters.

When utilizing NMR to produce images and chemical spectra, a technique is employed to obtain NMR signals from specific locations in the subject. Typically, the region to be imaged (region of interest) is scanned using a sequence of NMR measurement cycles that vary according to the particular localization method being used. To perform such a scan, it is, of course, necessary to elicit NMR signals from specific locations in the subject. This is accomplished by employing magnetic fields ($G_x$, $G_y$, and $G_z$) which have the same direction as the polarizing field $B_0$, but which have a gradient along the respective x, y and z axes. By controlling the strength of these gradients during each NMR cycle, the spatial distribution of spin excitation can be controlled and the location of the resulting NMR signals can be identified from the Larmor frequencies typical of the local field. The acquisition of the NMR signals is referred to as sampling k-space, and a scan is completed when sufficient NMR cycles are performed to fully or partially sample k-space. The resulting set of received NMR signals are digitized and processed to reconstruct the image using various reconstruction techniques.

To generate a magnetic resonance ("MR") anatomical image, gradient pulses are typically applied along the x, y and z-axis directions to localize the spins along the three spatial dimensions, and MR signals are acquired in the presence of one or more readout gradient pulses. An image depicting the spatial distribution of a particular nucleus in a region of interest of the object is then generated, using known reconstruction and post-processing techniques. Typically, the hydrogen nucleus (1H) is imaged, though other MR-detectable nuclei may also be used to generate images.

Motion occurs during imaging and image-guided therapies due to periodic, semi-periodic (e.g., respiration, peristalsis, cardiac) and non-periodic (e.g., cough, sneeze, bulk movement) activities. Since motion can introduce significant imaging artifacts or unwanted treatment effects, motion is often tracked using cameras, body devices (e.g., bellows), or imaging. Specifically, motion-induced errors can be especially critical for interventional treatments, such as radiotherapy, focal ablation or targeted needle-based procedures, in which deviations of target position can produce appreciable complications to critical structures unless taken into account. Therefore, motion is often tracked and used prospectively or retrospectively to acquire and reconstruct images, as well as compensate for motion during various therapies. However, retrospective approaches are not applicable to real-time applications. In addition, prospective approaches can introduce undesired latencies.

Therefore, there is a need for improved systems and methods implementing motion tracking and prediction.

SUMMARY

The present disclosure overcomes the drawbacks of previous technologies by providing a system and method directed to motion prediction in dynamic imaging, such as magnetic resonance imaging ("MRI"). In particular, a novel motion prediction framework is introduced herein that can provide accurate and real-time motion information. As will be described, the motion prediction framework incorporates image-based motion tracking with an adaptive filtering technique and a multi-rate data fusion method that can be used to identify and predict motion. This approach overcomes latencies and allows for accurate and real-time feedback regarding motion of a target to be provided to clinicians, imaging systems, as well as automated or robotic interventional systems.

In accordance with one aspect of the disclosure, a method for predicting motion of a target using imaging is provided. The method includes receiving image data, acquired using an imaging system, corresponding to a region of interest ("ROI") in a subject, and generating a set of reconstructed images from the image data. The method also includes processing the set of reconstructed images to obtain motion information associated with a target in the ROI, and utilizing the motion information in a motion prediction framework to estimate a predicted motion of the target. The method further includes generating a report based on the predicted motion.

In accordance with another aspect of the disclosure, a method for predicting motion of a target using imaging is provided. The method includes receiving image data, acquired using an imaging system, corresponding to a region of interest ("ROI") in a subject, and generating a set of multi-rate images from the image data. The method also includes processing the set of multi-rate images to obtain motion information associated with a target in the ROI, and utilizing the motion information in a motion prediction framework to estimate a predicted motion of the target. The method further includes generating a report based on the predicted motion.

In accordance with yet another aspect of the disclosure, a system for predicting motion of a target using imaging is provided. The system includes an input in communication with an imaging system configured to acquire image data from a subject correspond to a region of interest ("ROI") in a subject. The system also includes at least one processor configured to receive the image data from the imaging system using the input, and reconstruct a set of images using the image data. The at least one processor is also configured to process the set of images to obtain motion information associated with a target selected in the ROI, and estimate, using a motion prediction framework, a predicted motion of the target using the motion information. The at least one processor is further configured to generate a report based on the predicted motion. The system further includes an output for providing the report.

The foregoing and other advantages of the invention will appear from the following description.

BRIEF DESCRIPTION OF THE DRAWINGS

The present invention will hereafter be described with reference to the accompanying drawings, wherein like reference numerals denote like elements.

FIG. 8A is an image showing an example motion phantom used to verify methods of the present disclosure.

FIG. 8B is an image showing an example graphical user interface, in accordance with aspects of the present disclosure.

FIG. 8C is a graphical illustration comparing error variance obtained using manual and algorithm-based motion tracking for different breathing patterns, in accordance with aspects of the present disclosure.

DETAILED DESCRIPTION

Imaging can provide real-time information about tissues and objects inside a subject's anatomy. Specifically, the motion of tissues and their surroundings is highly useful to guide a physician's decision on treatment options, as well as to facilitate automation and control of treatment. Therefore, image guidance techniques, such as fluoroscopic or other radiation-based imaging methods, are often utilized to assess motion. Alternatively, magnetic resonance imaging ("MM") avoids ionizing radiation and provides enhanced soft-tissue contrast. However, conventional image guidance techniques based on MRI utilize low frame rates, often provide limited motion information, and introduce latencies. In addition, MRI-guided interventions in the certain regions of a subject's anatomy, such as the upper abdomen, are challenged by limited access to the subject inside the scanner bore. On the other hand, surrogate-based tracking techniques can achieve low latency, but are often limited in spatial resolution and require external measurement systems or markers.

By contrast, the present disclosure solves the shortcomings of previous technologies by introducing a novel approach capable of motion prediction in dynamic imaging. Specifically, a motion prediction framework is described, which incorporates image-based motion tracking, adaptive filtering, and modeling to provide motion information in real-time. In some aspects, a multi-rate data fusion technique is also utilized to increase the temporal rate of the feedback. Furthermore, and unlike current technologies, the present disclosure proves a platform that can process real-time MR images to provide motion feedback to clinicians or automation equipment.

Although the discussion that follows refers specifically to MRI, the present approach may be readily extended to other imaging modalities including X-ray, computed tomography ("CT"), positron emission tomography ("PET"), ultrasound ("US"), optical imaging, and other imaging modalities.

Figure 1:
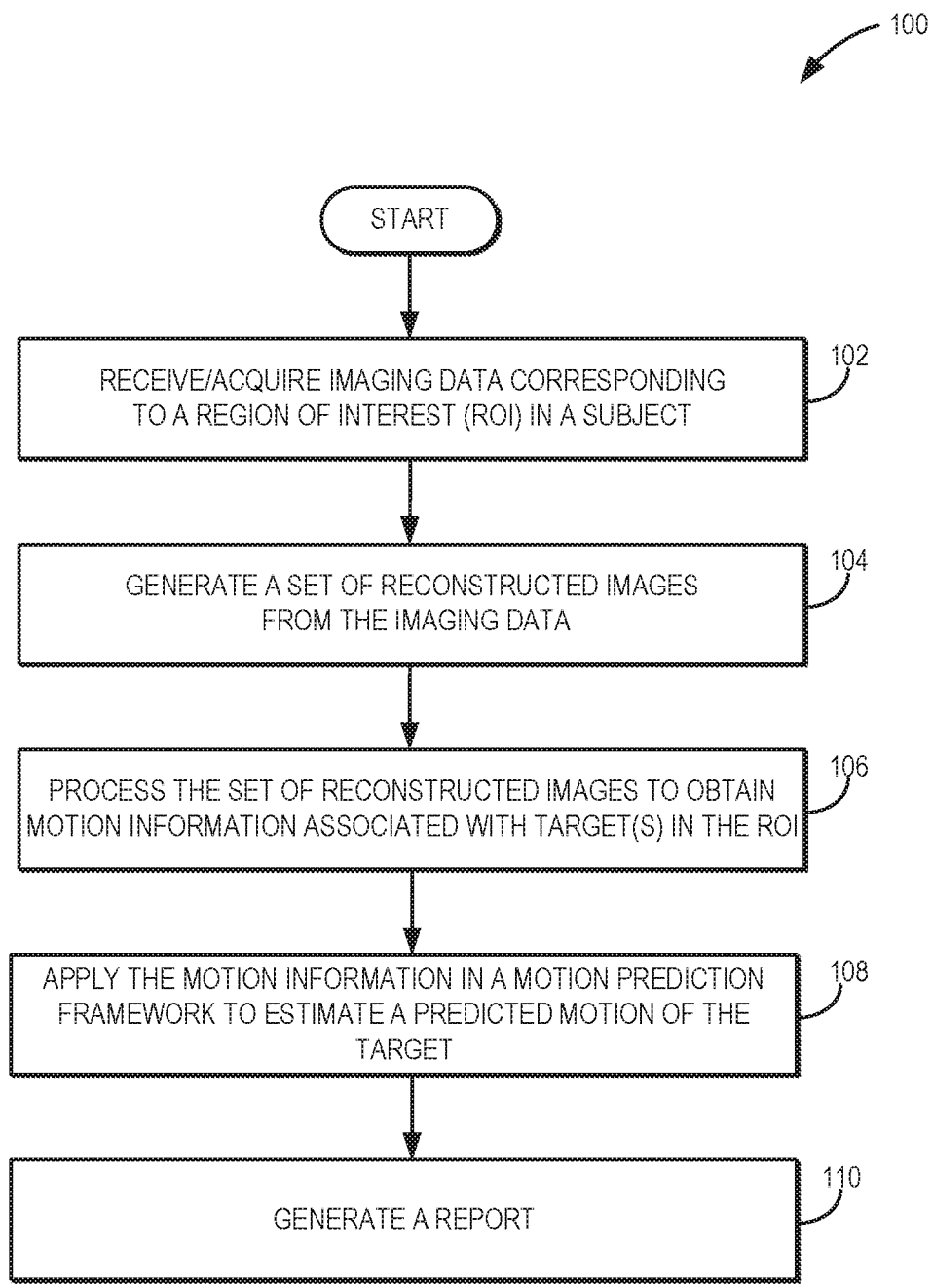
FIG. 1 is a flowchart setting forth steps of a process, in accordance with aspects of the present disclosure.

Turning particularly to FIG. 1, a flowchart setting forth steps of a process 100 for generating motion information using imaging, in accordance with aspects of the present disclosure, is shown. The process 100, or various steps therein, may be carried on or using any suitable device, apparatus or system, such as the systems described with reference to FIGS. 2 and 7. In some implementations, the steps of the process 100 may be performed by one or more processors configured to execute programming or instructions stored in non-transitory computer readable media. The processor(s) may be include general-purpose processors, as well as application-specific processors having programming or executable instructions hardwired therein.

The process 100 may begin at process block 102 with receiving image data corresponding to a region of interest ("ROI") in a subject. For example, the ROI may include an abdominal region, a pulmonary region, a head and neck region, and other anatomical regions. The image data may include one-dimensional ("1D"), two-dimensional ("2D"), three-dimensional ("3D") image data, and combinations thereof. The image data may include magnetic resonance imaging ("MM") data, as well as X-ray data, computed tomography ("CT") data, positron emission tomography ("PET") data, ultrasound ("US") data, or optical image data. In some aspects, image data may be acquired at process block 102 for a pre-determined period of time using an imaging system. The period of time may be sufficiently long to capture known motion features, such as periodic and non-periodic movements. The image data may be acquired in substantially real-time.

Then, at process block 104, a set of reconstructed images may be generated from the received or acquired image data. In some aspects, the reconstructed images may be multi-rate images. For instance, the set of reconstructed images may include a first set of images having a low temporal rate ("LTR"), or frame rate, and a high spatial resolution ("HSR"), and a second set of images having a high temporal rate ("HTR") and a low spatial resolution ("LSR"), or variations thereof. In generating the set of reconstruction images, various reconstruction algorithms may be used depending upon the specific image data utilized. In some aspects, the received or acquired image data, or images reconstructed therefrom, may be downsampled, upsampled, decomposed, combined, or otherwise processed to generate various sets of images with desired temporal and spatial resolutions. For example, an image dataset may be used to generate low frame rate images, while a subset of the image dataset may be used to generate high frame rate images.

In some aspects, various supplementary measurements from other sensor inputs, such as electrocardiogram ("ECG") measurements, respiratory bellows measurements, and others, may be acquired and utilized to decompose or combine received or acquired image data, or images reconstructed therefrom. The supplementary measurements may also be used in combination with the image data for motion tracking and prediction. For instance, a multi-rate adaptive filtering technique may utilize generated motion waveforms in combination with the supplementary measurements to estimate motion state variables.

At process block 106, the set of reconstructed images may then be processed to obtain motion information associated with at least one target (e.g. an organ, tissue, and so on), or target feature (e.g. a portion of the organ or tissue), in the ROI. Specifically, the reconstructed images may be registered to a reference image using various registration algorithms. The target, or target feature, may be selected manually, or using various automated or semi-automated segmentation algorithms. Then, a motion waveform indicative of motion of the target or target feature may be generated by analyzing the position of the target or target feature using temporally ordered reconstructed images. Other motion tracking algorithms may also be used.

In some aspects motion information may be obtained from real-time images using a multi-resolution intensity-based least squares registration algorithm. Specifically, low and high resolution images may be registered to a reference image, and motion information may then be extracted by analyzing the registered images. As such, a number of motion waveforms may be obtained for each target or target feature. As described, different sets of images may have different temporal rates and spatial resolutions. For instance, a first motion waveform (e.g. low resolution waveform) may be obtained using a first set of images (e.g. LTR images), while a second motion waveform (e.g. high resolution waveform) may be obtained from the second set of images (e.g. HTR images). As such, the resulting motion waveforms may have different temporal resolutions, and extend over different durations. In some aspects, motion waveforms may be combined to generate one or more combined motion waveforms. In addition, motion waveforms obtained may be temporally shifted, or delayed relative to one another.

Then, at process block 108, a motion prediction framework may utilize the motion information obtained at process block 106 to estimate a predicted motion of one or more targets, or target features. In particular, the predicted motion reflects anticipated or future movement(s) the target(s) at one or more points in time. As will be described, obtaining the predicted motion may include performing an adaptive filtering technique to estimate a motion state variable. An example adaptive filtering technique includes applying a Kalman filtering technique. The predicted motion may then be estimated using the adaptive filter and the motion state variable. In some applications, the motion state variable may be estimated before or during the performance of a medical procedure or intervention.

In some aspects, an adaptive calibration may be performed at process block 108 to update the model parameters of the adaptive filter and the motion state variable when a motion prediction error exceeds a predetermined threshold. The predetermined threshold can reflect an acceptable motion error, which may depend upon the specific target, target location, treatment being provided, and other technical or medical factors. To this end, a comparison between measured motion and predicted motion may also be performed at process block 108. In one example, the adaptive calibration of the adaptive filter may be performed using an expectation maximization ("EM") technique, although other techniques are possible.

A report may then be generated at process block 110. In some implementations, the report may be provided to an output, e.g. display or graphical user interface, either intermittently or in substantially real-time. The report may have any form, and include various information. In one example, the report may include motion information, such as measured and predicted motion, in the form of real-time waveforms, absolute or average displacement, velocity, and acceleration values, motion trajectories, motion directions, motion prediction errors, confidence intervals, and so on. The report may include images (e.g. real-time images), as well as other measurements, numerical or visual indicators (e.g. tracked targets).

The report may also include information, instructions or control signals for use in controlling an imaging system (e.g. an MRI system) or treatment system (e.g. a robotically- or computer-controlled treatment device or apparatus). To this end, the report may include information actionable by the imaging system or interventional system. For example, the report may include motion information, which may be analyzed by the interventional system and translated into operational parameters. Similarly, motion information may be analyzed by the imaging system to adapt image acquisition parameters (e.g. imaging planes, image acquisition timings, and so on), as well as image reconstruction and processing methods. Alternatively, the report may include instructions in the form of control signals executable by, and controlling the operation of, the imaging system and/or interventional system.

Figure 2:
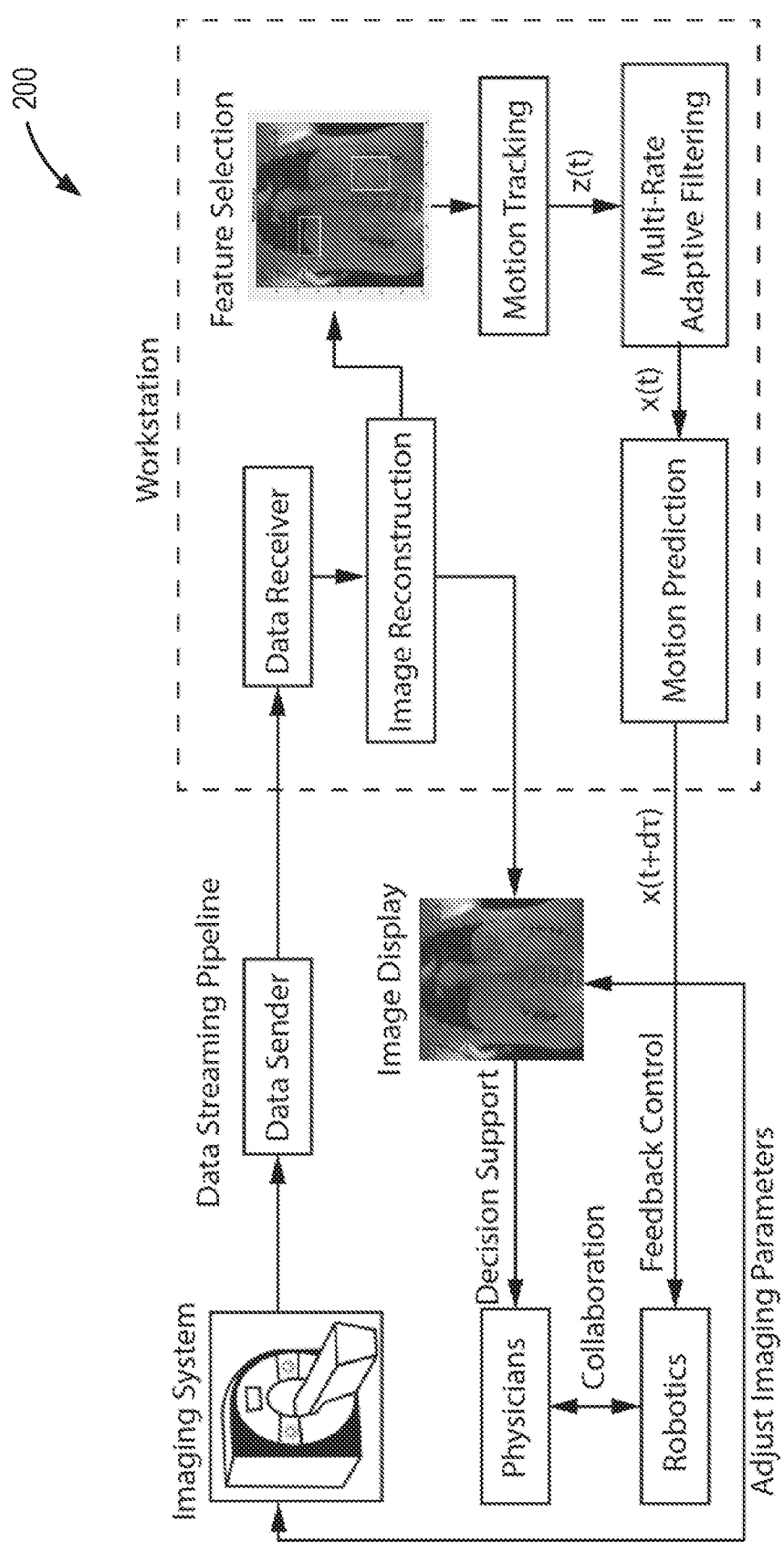
FIG. 2 is a schematic of an example system, in accordance with aspects of the present disclosure.

In one non-limiting example, the above-described process 100 can be implemented using a data-streaming and processing pipeline, as illustrated visually in the schematic 200 shown in FIG. 2. The process may begin with acquiring image data (e.g. k-space MIll data), either intermittently or continuously using an imaging system (e.g. MIll scanner). The image data is then transferred to a workstation for subsequent processing. Specifically, the data is directed through a data streaming pipeline, which consists of a data sender and a data receiver residing on the workstation. The received data is reconstructed, and the resulting images may be provided to an image display in support of physician decision. The images may be reconstructed using various image reconstruction algorithms, and with different temporal and spatial resolutions. As shown in FIG. 2, reconstructed images may also be analyzed to obtain motion information, which may then be provided as feedback to robotic and other interventional systems. In some aspects, the motion information may also be used to adjust imaging parameters.

To obtain motion information, a reference image may be selected from a set of reconstructed images. Then, various targets or target features may then be defined on the reference image, either manually, semi-automatically or automatically. The displacements or motion waveforms of the targets or features may be extracted using image registration (e.g., template matching). In some aspects, a multi-resolution intensity-based least square registration algorithm can be applied to solve the problem with less computational cost. For instance, coarse to fine scale images $(s_d)$ may be registered to the reference image $(s_r)$ as follows:

$$z = \operatorname{argmin} \sum_{w=0, h=0}^{w=W, h=H} |I_d(w, h) - I_r(w, h)|^2 \quad \text{Eqn. (1)}$$

The tracking results of a given target or feature, z(t), i.e. motion waveform, may then be processed using an adaptive filtering technique to obtain an estimation of a state motion variable x(t), which may include displacement and velocity information of a selected target. The state motion variable can then be used to estimate a predicted motion of the target(s). Adaptive filtering reduces tracking error caused by image noise and artifacts. In one example, a Kalman filtering ("KF") technique may be utilized as the adaptive filtering technique. Kalman filters are a simple recursive solution for state estimation that can provide accurate and real-time motion information, and can reduce computation complexity. Reliable characterization of motion and measurement stochastic model parameters is important for the estimation. Therefore, for an initial calibration, an expectation maximization ("EM") algorithm can be used to take the previous motion results as input to estimate the most likely value of the model parameters for KF. For example, to model periodic motion, an approximate linear motion system can be derived using a sinusoidal model, as follows:

$$y = A \sin(2\pi f t + \varphi) + B$$

$$x_k = F x_{k-1} + w_k \text{ with } w_k \sim N(0, Q) z_k = H x_k + v_{k+1} \text{ with } v_k \sim N(0, R) \quad \text{Eqn. (2)}$$

Estimation of the motion and uncertainty parameters of stochastic motion can be updated in a predictor-corrector algorithm, as follows:

$$\mu_k = F x_{k-1} + K(z_k - H \mu_{k-1}) P_{k+1} = (1 - K_k H)(A P_{k-1} A^T Q)$$

Kalman Gain: $K_{k+1} = (A P_{k-1} A^T + Q) H (H (A P_{k-1} A^T + Q) H^T + R)^{-1}$ \quad Eqn. (3)

Using the motion state variable at time t, a predicted motion state at t+di can be calculated based on a transition model of the linearized motion system according to:

$$\mu_{k+n}(d\tau) = H F^{d\tau/dt} \mu_k \quad \text{Eqn. (4)}$$

Figure 3A:
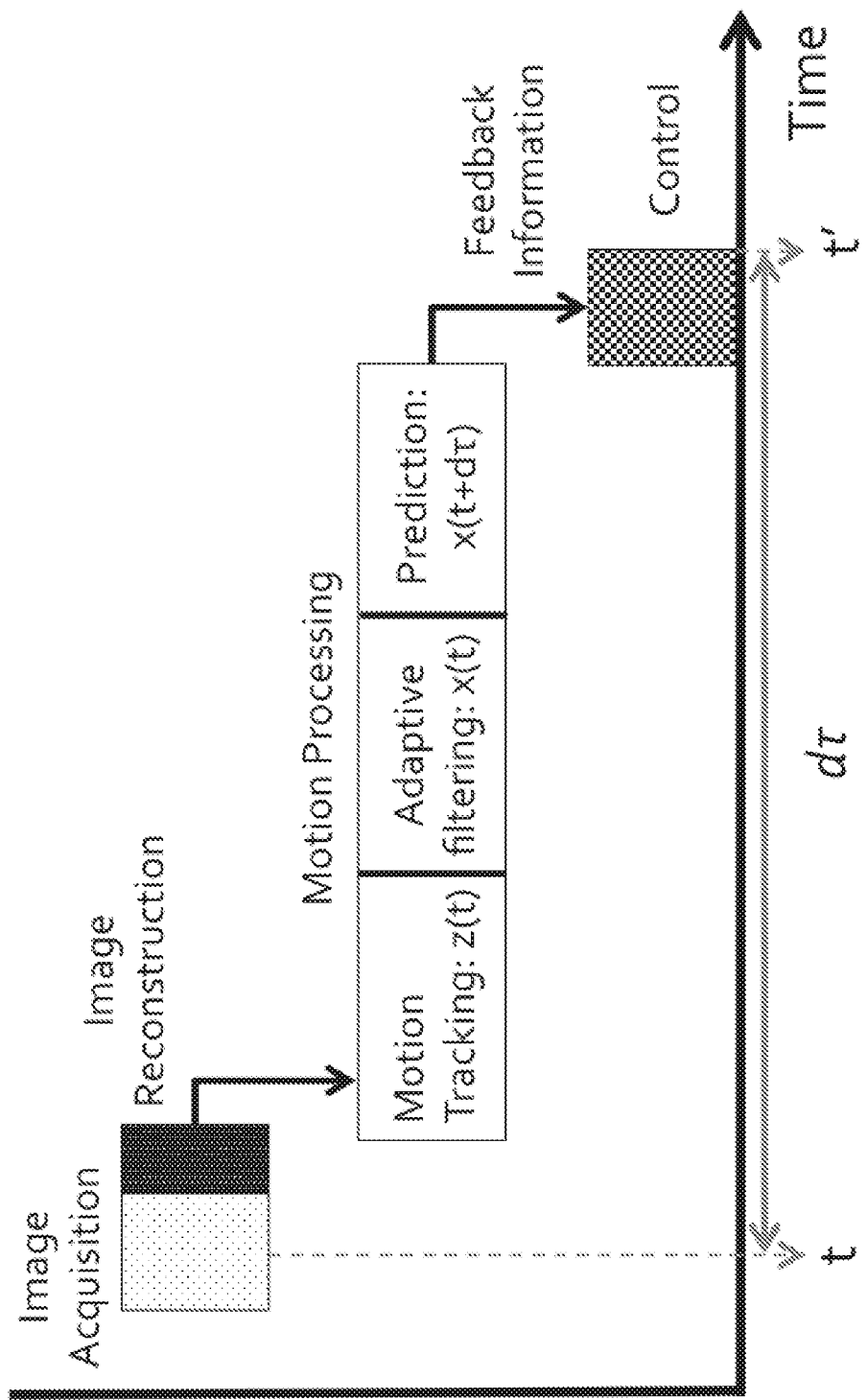
FIG. 3A is a diagram illustrating a motion prediction process, in accordance with aspects of the present disclosure.

The predicted motion state can then be utilized to obtain an estimate of predicted motion, which can be provided as feedback either to the imaging system for adapting image data acquisition parameters, or to robotics or hardware controlling an interventional system, as shown in FIG. 2. The predicted motion can also be used to update an image display. The timing for generating motion information from images with various temporal resolution, in accordance with aspects of the present disclosure, is further illustrated in FIGS. 3A and 3B.

Figure 4:
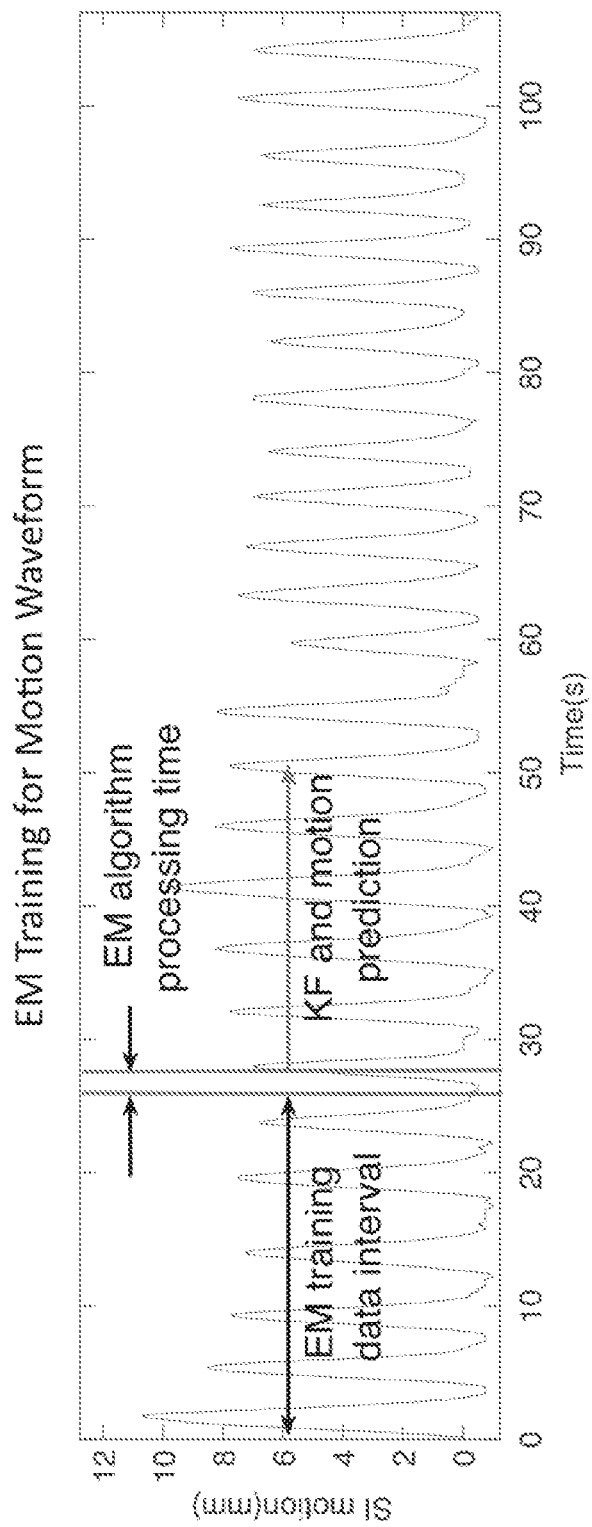
FIG. 4 is a graph showing the expectation maximization ("EM") technique and Kalman filtering technique for motion prediction, in accordance with aspects of the present disclosure.

As mentioned, the optimal mean (μ) and covariance (P) of the state variable x(t) may be derived based on the system parameters (F, H) and the uncertainty covariance (Q, R). The EM algorithm can utilize training data to calibrate the most likely value of the system parameters, as shown in the example of FIG. 4. In practice, an adaptive calibration may also be implemented to trigger EM calibration when a motion prediction error exceeds a threshold. As described, this may involve comparing measured motion with predicted motion.

Figure 3B:
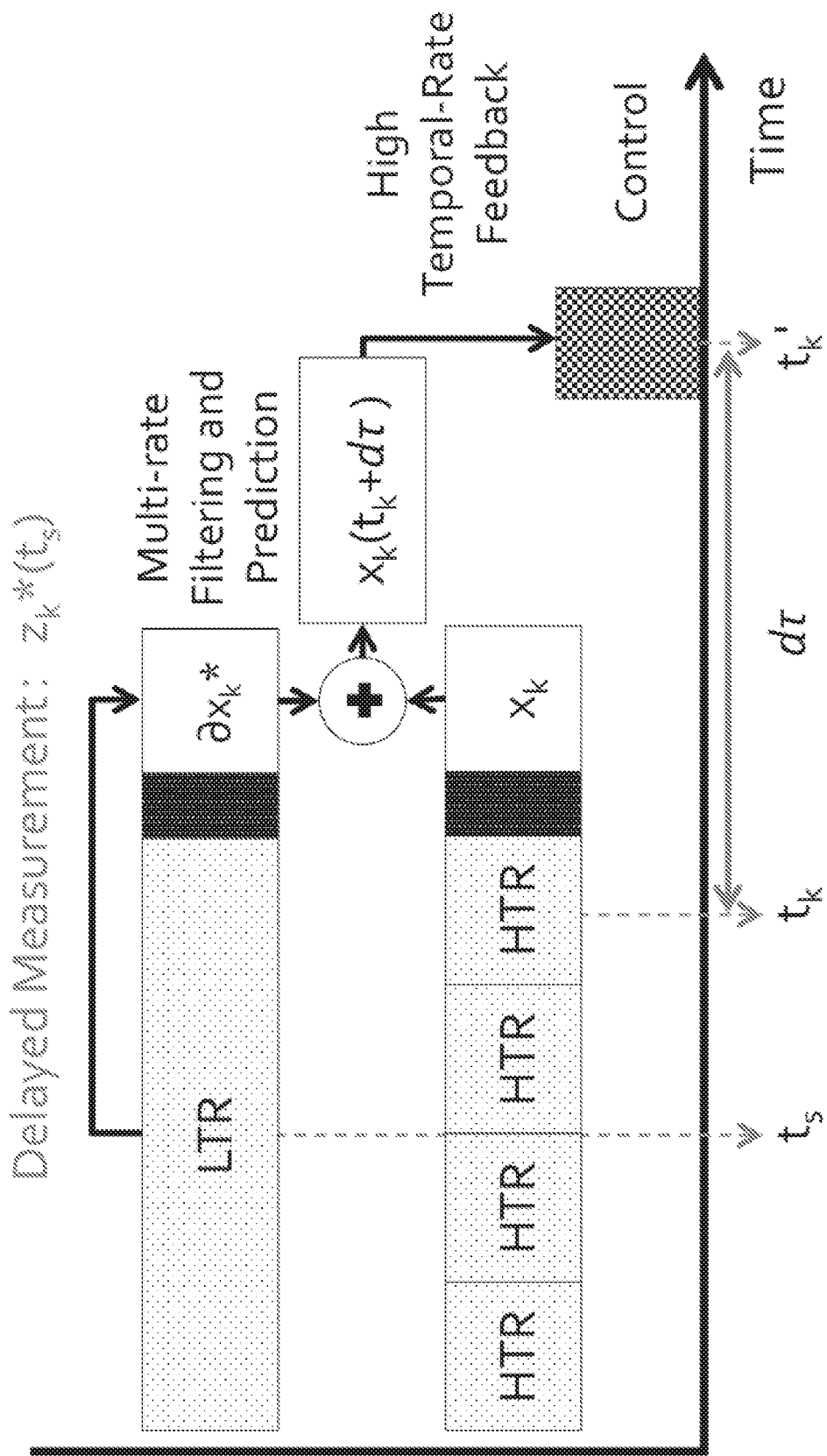
FIG. 3B is a diagram illustrating a multi-rate motion prediction process, in accordance with aspects of the present disclosure.
Figure 3C:
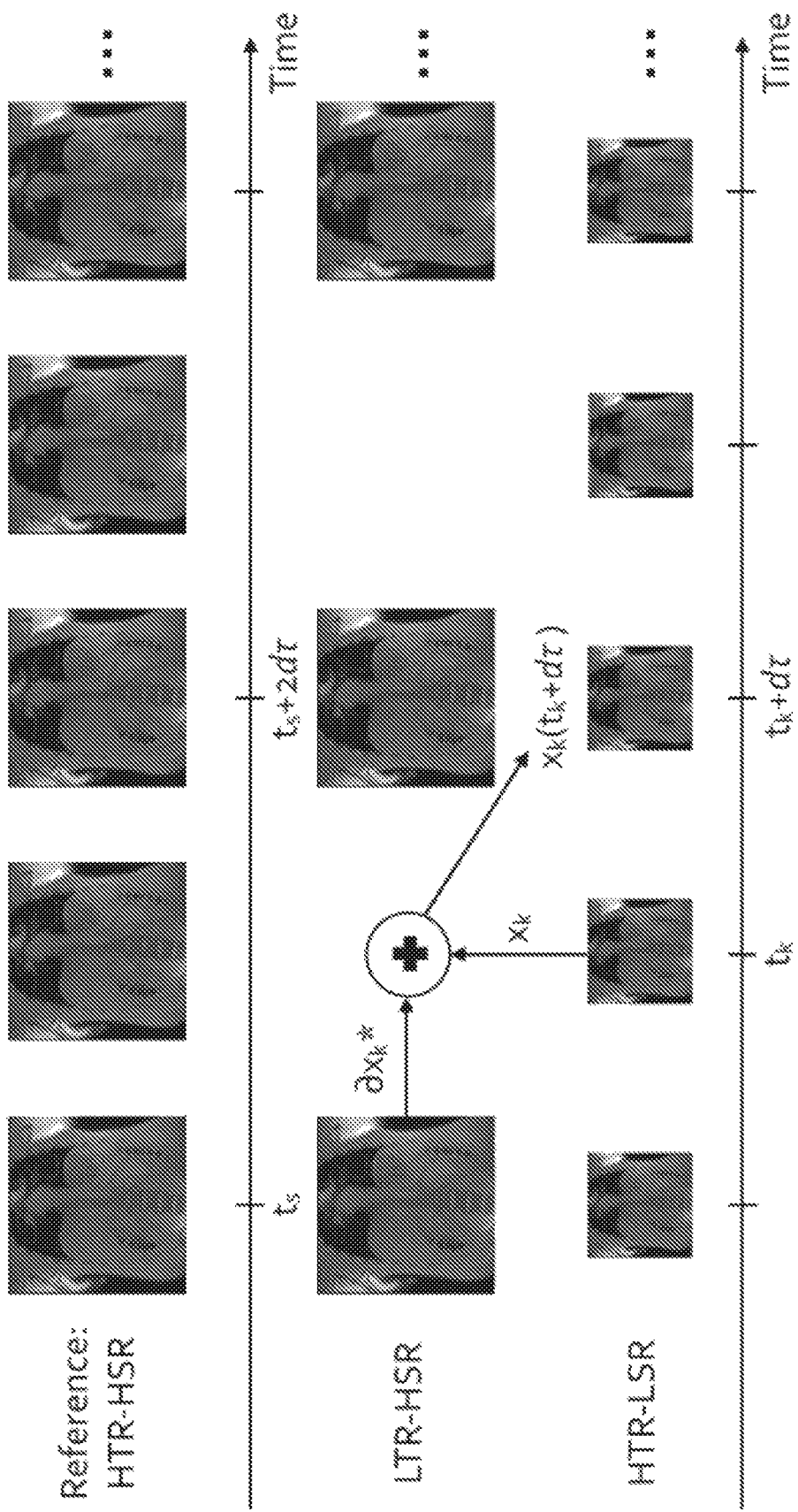
FIG. 3C is an illustration of the multi-rate motion prediction process of FIG. 3B.

The accuracy of an adaptive filtering described is dictated by the image quality of the acquired images. To achieve both continuous and accurate motion prediction, in some aspects, LTR images having high image quality can be used to generate LTR motion tracking information as delayed measurements. These results may then be fused or combined with HTR results to improve optimality of the estimation and the accuracy of tracking. This is illustrated in FIGS. 3B and 3C.

Therefore, a multi-rate adaptive filtering technique, e.g. a multi-rate Kalman filtering ("MRKF") technique, can be used to combine LTR motion tracking results with the HTR tracking results based on, for example, Alexander's algorithm, as follows:

$$x^*_k = M_* K(z^*_k - x_s) + x_k M_* = \Pi_{i=0}^{N-1}(1 - \operatorname{diag}(K_{k-1})) F \quad \text{Eqn. (5)}$$

The present motion prediction framework can therefore take advantage of higher accuracy of tracking results and model parameters to improve the motion information feedback. In particular, the MRKF approach predicts motion with a higher accuracy as compared to results obtained solely from LTR images, because the latency is reduced. In addition, the predicted motion is also more accurate compared to results obtained solely from HTR images, because, even though the latency might be substantially the same, the tracking error would be reduced by including LTR results into the state estimation.

Figure 5:
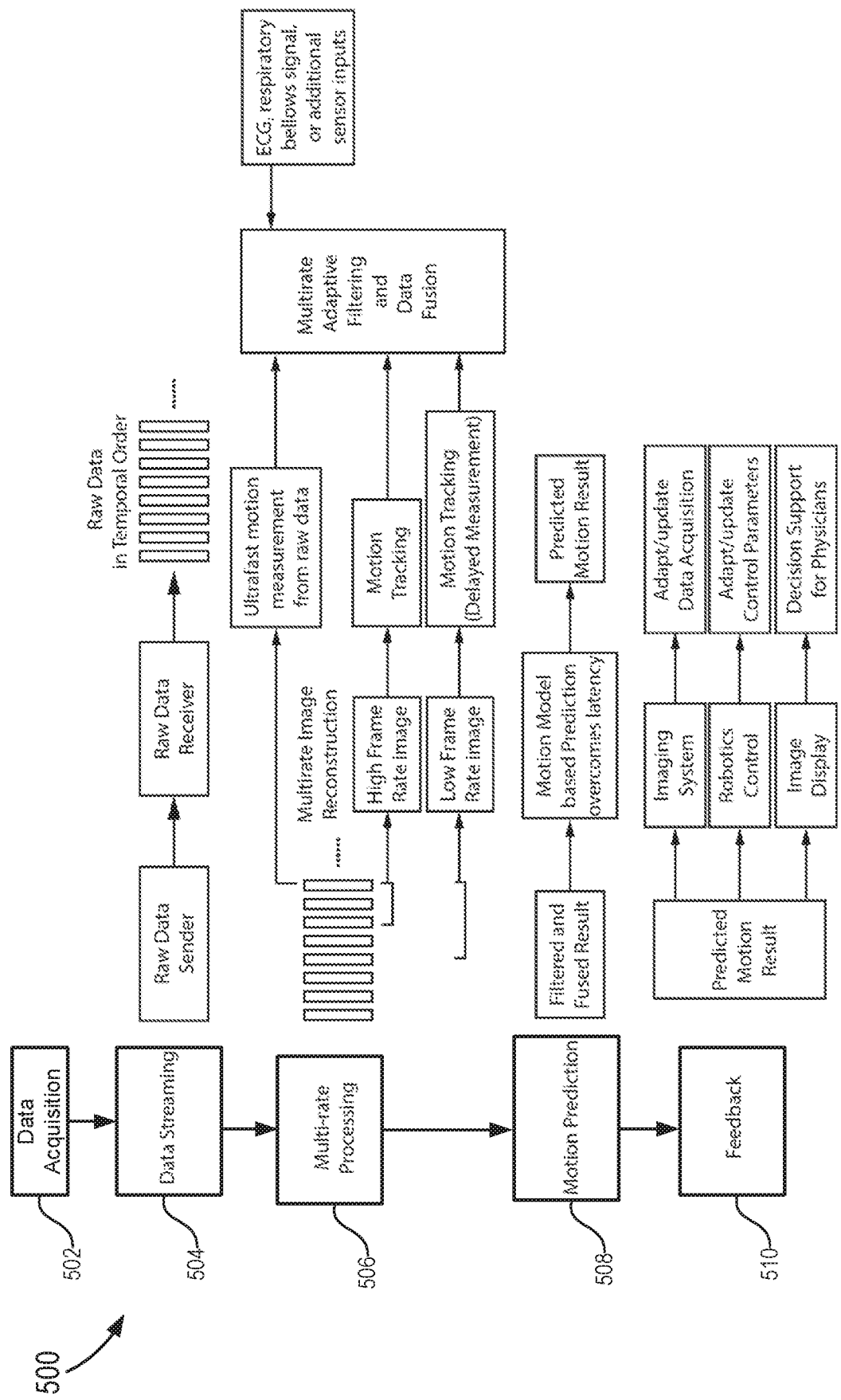
FIG. 5 is a flowchart setting forth steps of a process, in accordance with aspects of the present disclosure.

Referring particularly to FIG. 5, a flowchart setting forth steps of a process 500 in accordance with aspects of the present disclosure. The process 500 may be carried on or using any suitable device, apparatus or system, such as the systems described with reference to FIGS. 2 and 7. As described, various steps of the process 500 may be carryout out using one or more processors in accordance with programming or executable instructions.

As shown, the process 500 may begin at step 502 with data acquisition carried out over a period of time. As examples, the data can include MR, x-ray, CT, PET, US optical and other image data. The image data may then be streamed at step 502 using a raw data sender and receiver. As shown, in some aspects, the raw data may be arranged in temporal order by the raw data sender, receiver, or both.

At step 506, a multi-rate processing may then be carried out, as indicated. The multi-rate processing may utilize the streamed raw data to generate ultrafast motion measurements. The streamed raw data may also be used to reconstruct images with different frame rates. In one non-limiting example, a dataset of streamed raw data may be used to generate low frame rate images (e.g. LTR images), while a subset or portion of the dataset may be used to generate high frame rate images (e.g. HTR images). The HTR images may be used to track motion in substantially real-time while the LTR images may be used produce delayed motion measurements. The various motion measurements, as well as additional sensor measurements (such as electrocardiogram, respiratory bellows, navigator signal, etc.), may then be used in a multi-rate adaptive filtering and data fusion, as indicated, to generate a filtered and fused motion result.

Figure 6:
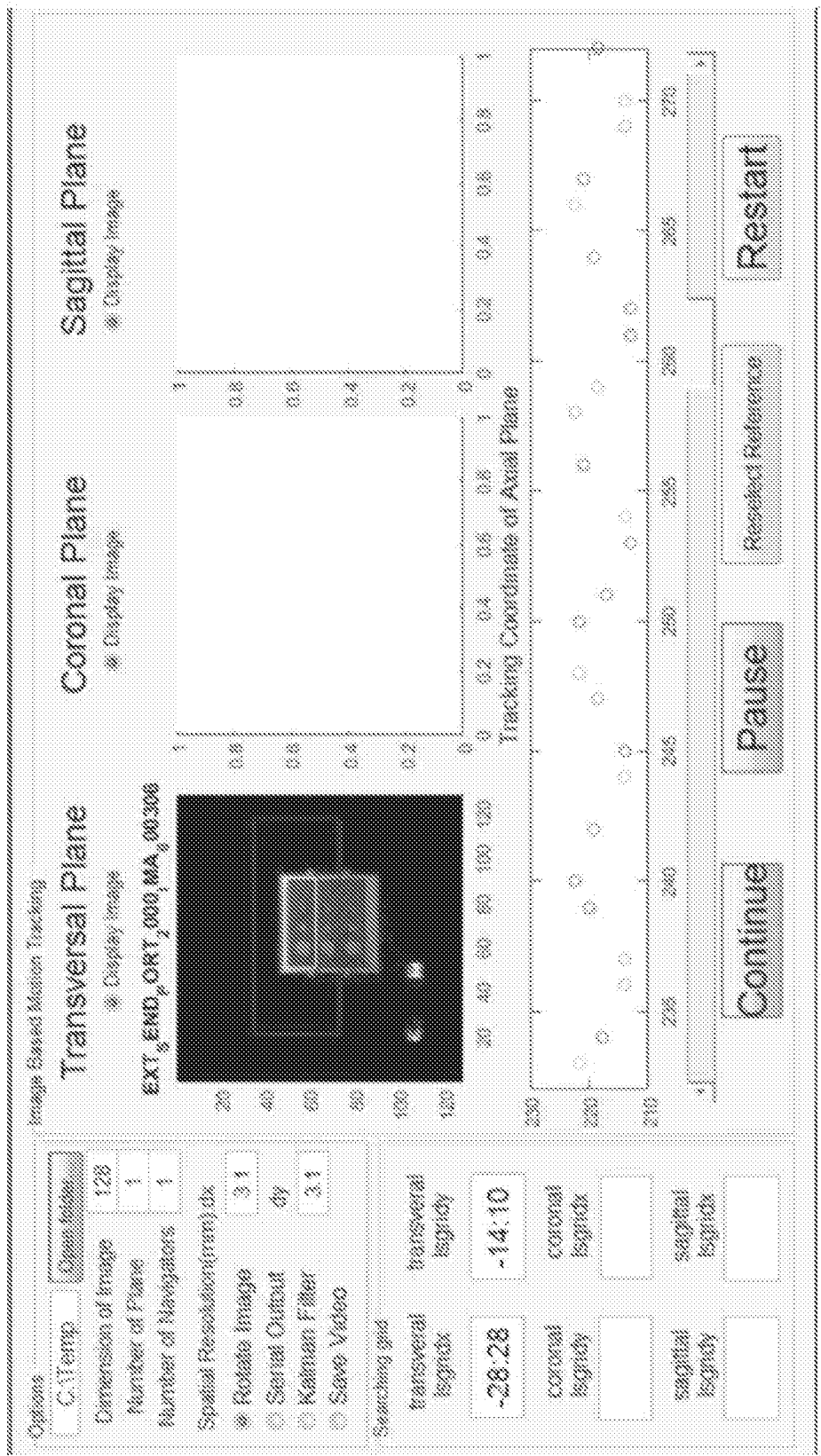
FIG. 6 is an example graphical user interface, in accordance with aspects of the present disclosure.

At step 508, the filtered and fused result may be used to generate a predicted motion, as described. And finally, the predicted motion can then be provided as feedback at step 510. As indicated in FIG. 5, feedback may be provided to an imaging system, to adapt or update imaging parameters or conditions. Feedback may also be provided to an automated or robotic system or hardware controlling interventional system, allowing adaptation or updating of control parameters. Furthermore, feedback can be provided to a physician or other clinician by way of an output or a graphical user interface (as shown in the example of FIG. 6).

Figure 7:
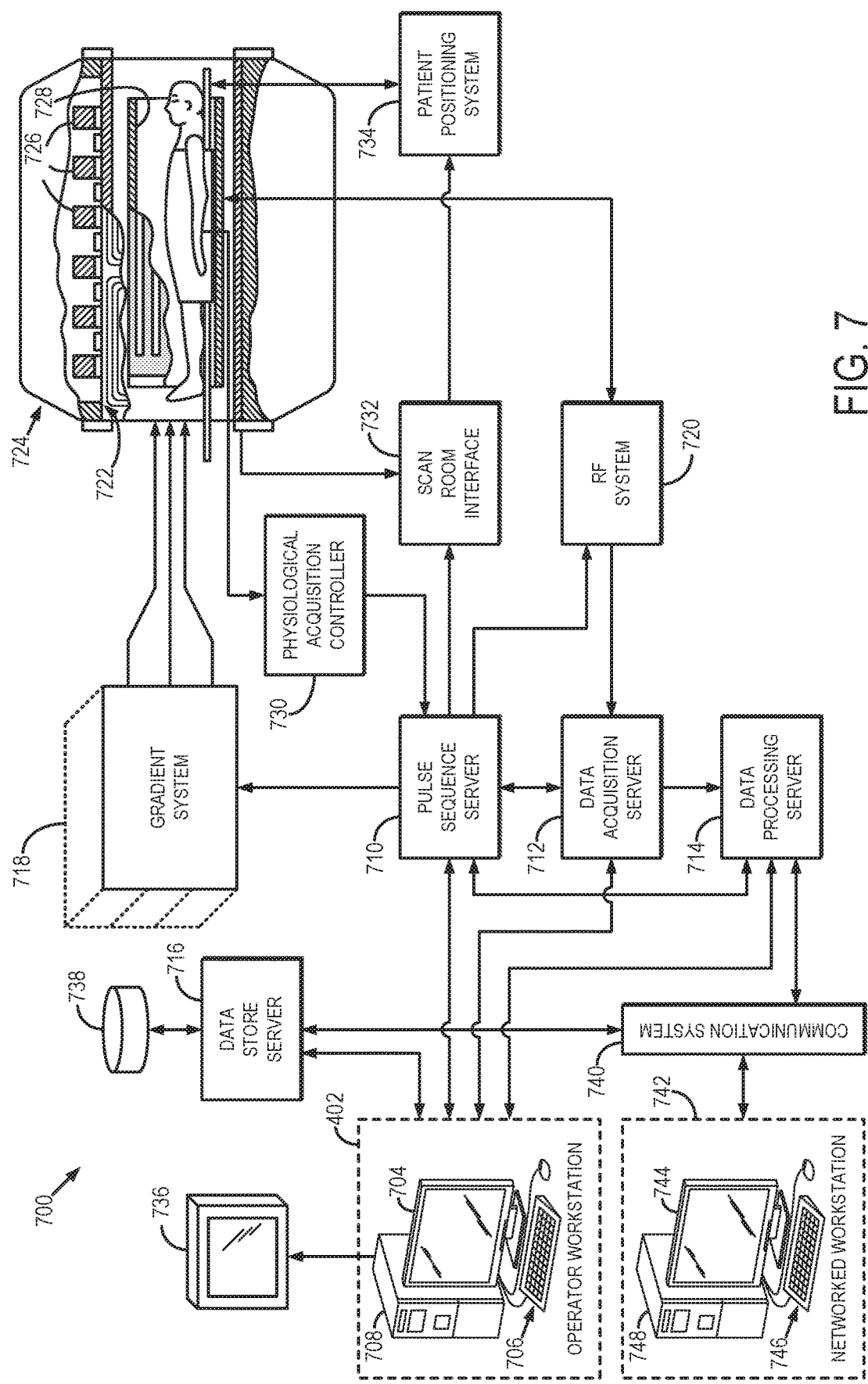
FIG. 7 is an example magnetic resonance imaging ("MRI") system, in accordance with aspects of the present disclosure.

Referring now particularly to FIG. 7, an example of an MRI system 700, in accordance with aspects of the present disclosure, is illustrated. The MRI system 700 includes a workstation 702 having a display 704 and a keyboard 706. The workstation 702 may include a processor 708, such as a commercially available programmable machine running a commercially available operating system. The processor 708 may also be an application-specific processor, as described. The workstation 702 provides the operator interface that enables scan prescriptions to be entered into the MM system 700. The workstation 702 is coupled to servers, including a pulse sequence server 710, a data acquisition server 712, a data processing server 714, and a data store server 716. The workstation 702 and each server 710, 712, 714, and 716 are in communication.

The pulse sequence server 710 functions in response to instructions downloaded from the workstation 702 to operate a gradient system 718 and a radiofrequency ("RF") system 720. Gradient waveforms necessary to perform the prescribed scan are produced and applied to the gradient system 718, which excites gradient coils in an assembly 722 to produce the magnetic field gradients $G_x$, $G_y$, and $G_z$ used for position encoding MR signals. The gradient coil assembly 722 forms part of a magnet assembly 724 that includes a polarizing magnet 726 and a whole-body RF coil 728.

RF excitation waveforms are applied to the RF coil 728, or a separate local coil (not shown in FIG. 7), by the RF system 720 to perform the prescribed magnetic resonance pulse sequence. Responsive MR signals detected by the RF coil 728, or a separate local coil, are received by the RF system 720, amplified, demodulated, filtered, and digitized under direction of commands produced by the pulse sequence server 710. The RF system 720 includes an RF transmitter for producing a wide variety of RF pulses used in MR pulse sequences. The RF transmitter is responsive to the scan prescription and direction from the pulse sequence server 710 to produce RF pulses of the desired frequency, phase, and pulse amplitude waveform. The generated RF pulses may be applied to the whole body RF coil 728 or to one or more local coils or coil arrays.

The RF system 720 also includes one or more RF receiver channels. Each RF receiver channel includes an RF preamplifier that amplifies the MR signal received by the coil 728 to which it is connected, and a detector that detects and digitizes the I and Q quadrature components of the received MR signal. The magnitude of the received MR signal may thus be determined at any sampled point by the square root of the sum of the squares of the I and Q components:

$$M = \sqrt{I^2 + Q^2} \qquad \text{Eqn. (6);}$$

and the phase of the received MR signal may also be determined:

$$\varphi = \tan^{-1}\left(\frac{Q}{I}\right). \qquad \text{Eqn. (7)}$$

The pulse sequence server 710 also optionally receives patient data from a physiological acquisition controller 730. The controller 730 receives signals from a number of different sensors connected to the patient, such as electrocardiograph ("ECG") signals from electrodes, or respiratory signals from a bellows or other respiratory monitoring device. Such signals are typically used by the pulse sequence server 710 to synchronize, or "gate," the performance of the scan with the subject's heart beat or respiration.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized MR signal samples produced by the RF system 720 are received by the data acquisition server 712. The data acquisition server 712 operates in response to instructions downloaded from the workstation 702 to receive the real-time MR data and provide buffer storage, such that no data is lost by data overrun. In some scans, the data acquisition server 712 does little more than pass the acquired MR data to the data processor server 714. However, in scans that require information derived from acquired MR data to control the further performance of the scan, the data acquisition server 712 is programmed to produce such information and convey it to the pulse sequence server 710. For example, during prescans, MR data is acquired and used to calibrate the pulse sequence performed by the pulse sequence server 710. Also, navigator signals may be acquired during a scan and used to adjust the operating parameters of the RF system 720 or the gradient system 718, or to control the view order in which k-space is sampled. In all these examples, the data acquisition server 712 acquires MR data and processes it in real-time to produce information that is used to control the scan.

The data processing server 714 receives MR data from the data acquisition server 712 and processes it in accordance with instructions downloaded from the workstation 702. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion, flow, or diffusion-weighted images.

Images reconstructed by the data processing server 714 are conveyed back to the workstation 702 where they are stored. Real-time images are stored in a data base memory cache, from which they may be output to operator display 712 or a display 736 that is located near the magnet assembly 724 for use by attending physicians. Batch mode images or selected real time images are stored in a host database on disc storage 738. When such images have been reconstructed and transferred to storage, the data processing server 714 notifies the data store server 716 on the workstation 702.

The MRI system 700 may also include one or more networked workstations 742. By way of example, a networked workstation 742 may include a display 744, one or more input devices 746 (such as a keyboard and mouse or the like), and a processor 748. The networked workstation 742 may be located within the same facility as the operator workstation 702, or in a different facility, such as a different healthcare institution or clinic. The networked workstation 742 may include a mobile device, including phones or tablets.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may be exchanged between the data processing server 714 or the data store server 716 and the networked workstations 742, such that the data or images may be remotely processed by a networked workstation 742. This data may be exchanged in any suitable format, such as in accordance with the transmission control protocol ("TCP"), the internet protocol ("IP"), or other known or suitable protocols.

Figure 9A:
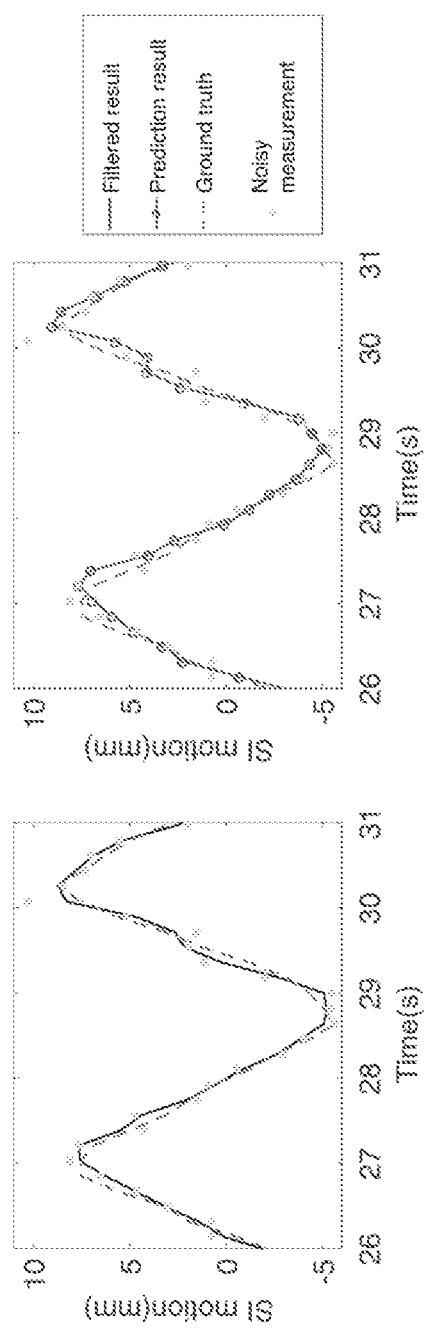
FIG. 9A are graphs showing filtered motion results, in accordance with aspects of the present disclosure.

By way of example, the present framework was implemented and interfaced to a 3T MRI system (Prisma, Siemens) for online processing (FIG. 2). An MR image-based navigation algorithm was used to track multiple targets with low computation overhead. The algorithm tracking performance was evaluated with an MR-compatible motion phantom (FIG. 8A). The algorithm tracking error was computed with respect to reference manual tracking results and used to calibrate measurement noise for KF simulations and processing (FIG. 8B). Upper abdominal images were acquired from healthy volunteers at 3T (Prisma, Siemens) with 5.6 frames/sec (dt=179 ms/frame), 2.5-mm spatial resolution, and 160×160 matrix size. Extracted motion waveforms were used as the ground truth and white Gaussian noise was added to simulate measurement noise (FIG. 9A).

Applying KFEM and EKF, the root mean square error (RMSE) of filtered motion at each time point and prediction at the next time point ($d\tau=dt$) were compared. Additionally, the tolerance of prediction error, i.e. percentage of prediction error greater than 2.5 mm (c (%)), was compared. The 2.5 mm tolerance represented less than 1 pixel error for these images and corresponded to the required accuracy for clinically relevant targets of greater than 5 mm diameter. KF processing time was negligible (5-10 ms). Since training data and processing for EM could increase latencies, 4 typical motion waveforms were analyzed. Also, the optimal amount of data for EM training was investigated by comparing the prediction error in the 400 time points after training.

MR images at high temporal rate (reference) were retrospectively undersampled to high temporal rate (HTR)-low spatial resolution (LSR) images and low temporal rate (LTR)-high spatial resolution (HSR) images, as illustrated in FIG. 3C. Simulations were also performed for MRKF prediction, and RMSE and ε were evaluated to compare with the KF prediction. The algorithm and manual tracking results are shown in FIGS. 3A-3B and FIGS. 8A-C, and Table 1 below. The average variance of the tracking error was 0.423 mm. (FIG. 8C) Since in vivo motion may have non-rigid components, the additive noise variance was increased to 1 mm in the KF simulations.

TABLE 1

Comparison of prediction performance.

| Motion Waveforms | Error metric | LTR-HSR prediction | HTR-LSR prediction | MRKF prediction |
|---|---|---|---|---|
| Normal Breathing | RMSE (mm) | 4.0904 | 2.7995 | 1.7854 |
|  | $\varepsilon_{2.5\ mm}$ (%) | 47 | 41.5000 | 22 |
| Deep Breathing | RMSE (mm) | 4.6105 | 3.9477 | 2.1489 |
|  | $\varepsilon_{2.5\ mm}$ (%) | 42.5 | 43.5 | 28 |

Figure 9B:
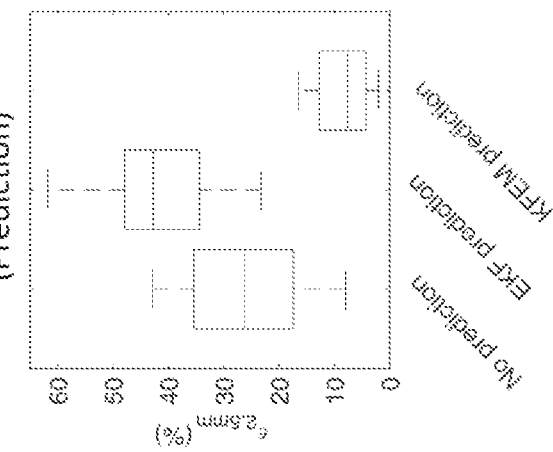
FIG. 9B are graphs comparing root mean square error ("RMSE") for motion results obtained in accordance with aspects of the present disclosure.
Figure 9B:
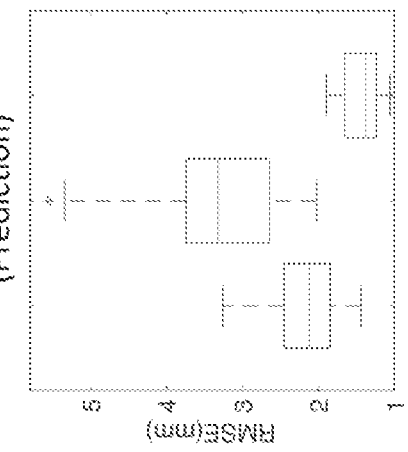
Figure 9B:
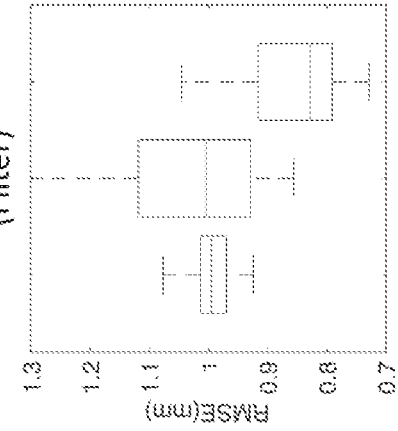

The filtered and 1-frame prediction result from KFEM had the least RMSE and prediction error, ε, as shown in FIG. 9B. As appreciated from these results, the present approach is more practical than EKF because the performance was less sensitive to initial parameter selection.

Figure 10:
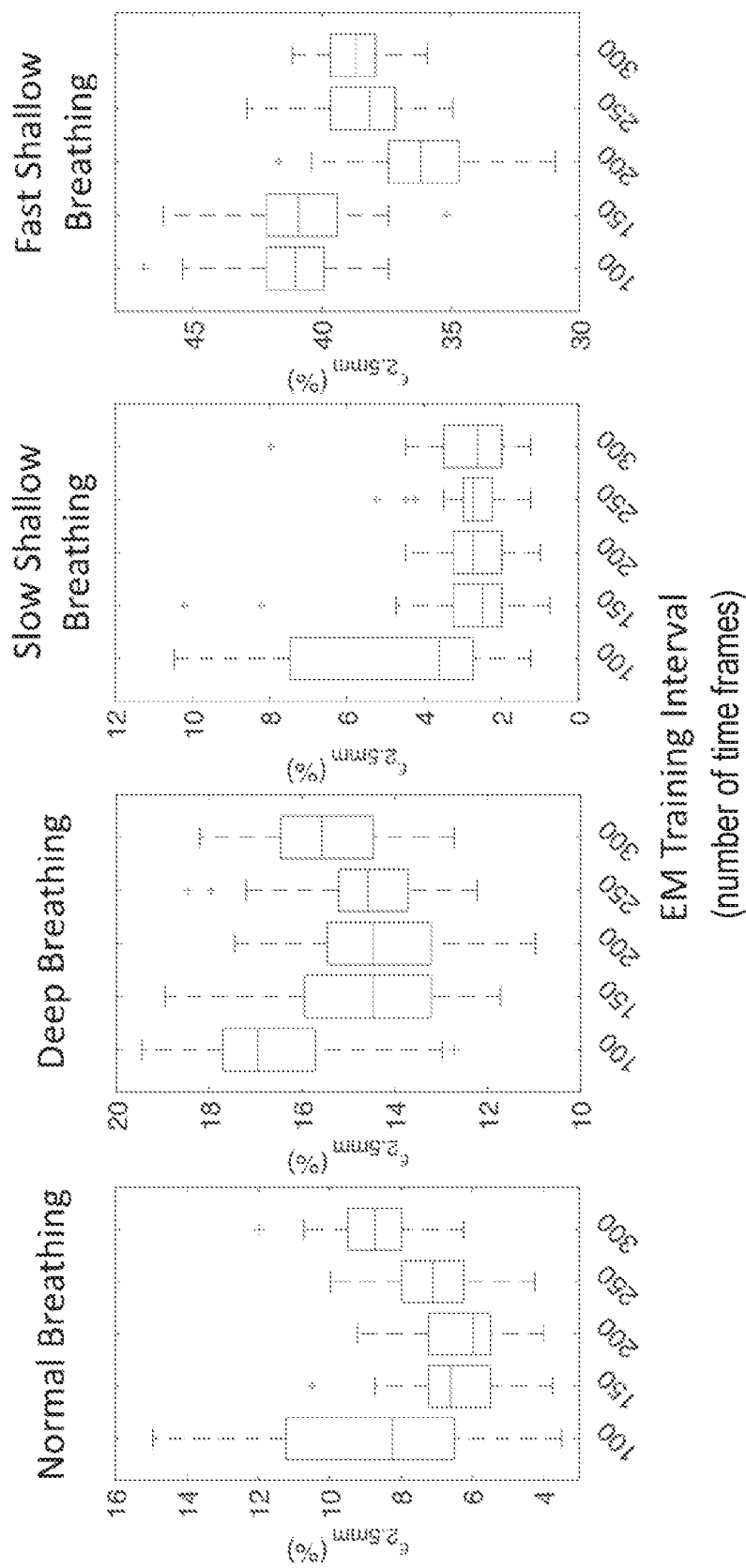
FIG. 10 are graphs comparing the tolerance of prediction error versus EM interval for different breathing patterns, in accordance with aspects of the present disclosure.

The optimal EM training interval in this example was observed to be about 150-200 frames (FIG. 10) and the average processing time was 0.8 s. To overcome training latencies, an adaptive strategy was implemented to trigger EM training when the motion prediction error exceeded a threshold. MRKF achieved lower prediction error than KF using only HTR-LSR or LTR-HSR (Table 1). This shows the potential of MRKF to improve the accuracy and temporal-rate of motion prediction by incorporating MR images with different rates, which can be obtained by reconstructing both LTR-HSR and HTR-LSR images from the same data (e.g., radial MRI).

In yet another example, an IRB-approved study was performed by acquiring 2D sagittal MR images from 3 healthy subjects using a 3T (Prisma, Siemens) scanner. The images were acquired using a spoiled gradient echo (GRE) golden angle (GA) radial sequence, which directly supports the reconstruction of multi-rate images from the same data. Each subject was instructed to perform normal, deep and shallow breathing (9 MRI datasets). Reconstruction windows (RW) were flexibly selected to generate images at different sampling rates. (FIG. 11).

Figure 11A:
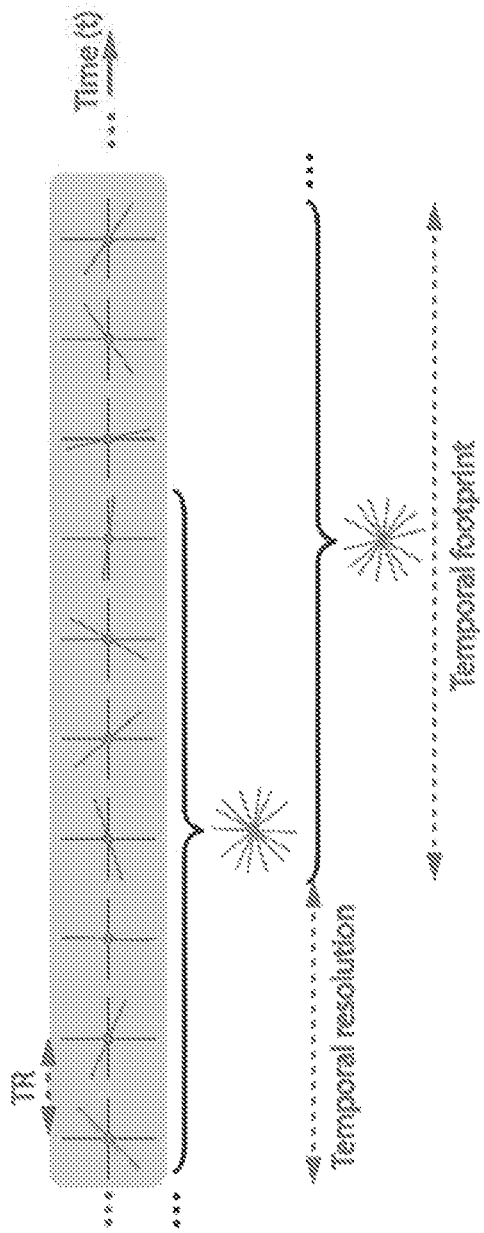
FIG. 11A is an illustration showing an example dynamic reconstruction approach based on Golden Angle ("GA") Radial MRI, in accordance with aspects of the present disclosure.
Figure 11B:
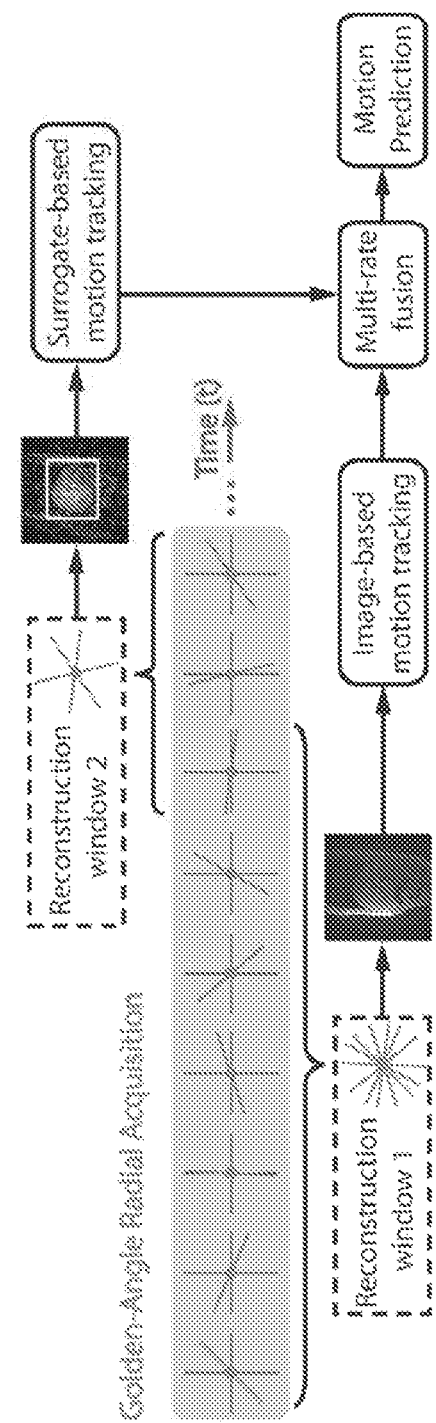
FIG. 11B is another graphical illustration showing the implementation of a GA radial acquisition, in accordance with aspects of the present disclosure.

The GA radial spokes were acquired using TR=4.68 ms and flip angle=70°. The field of view (FOV) was 300 mm×300 mm. (FIG. 11A). From reconstruction window 1 (RW1), 70 spokes were reconstructed with temporal footprint of 328 ms and sliding-window temporal resolution of 131 ms to generate images with spatial resolution of 1.56 mm×1.56 mm for image-based motion tracking of target tissue features. From RW2, 14 spokes were reconstructed with temporal footprint and temporal resolution of 66 ms to generate images with low spatial resolution of 4.84 mm×4.84 mm, which were used to extract the overall liver motion as the surrogate signal. (FIG. 11B).

Figure 12A:
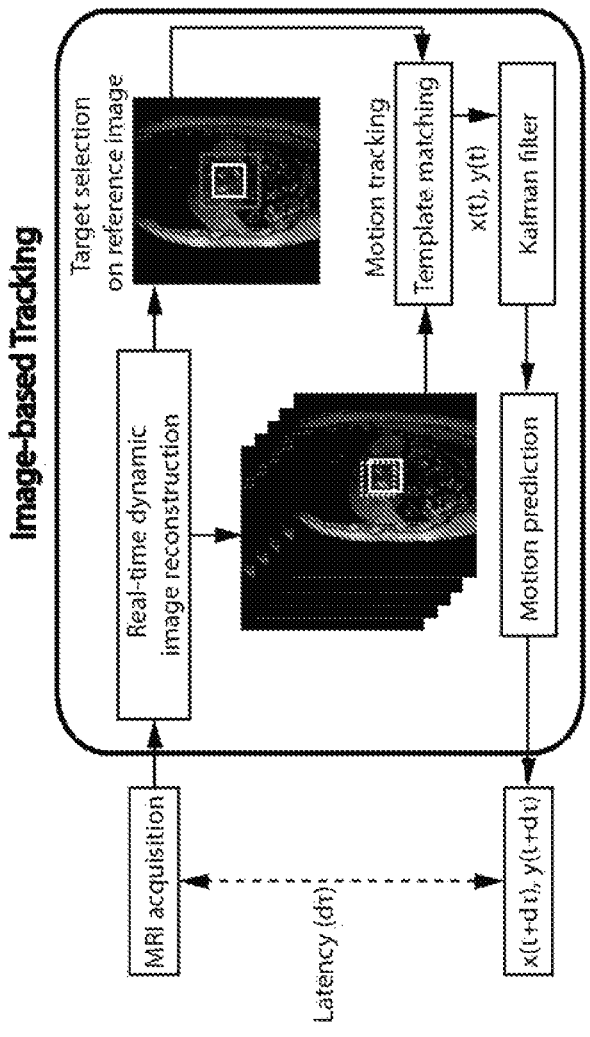
FIG. 12A is a graphical illustration showing steps of a process for motion prediction, in accordance with aspects of the present disclosure.
Figure 12C:
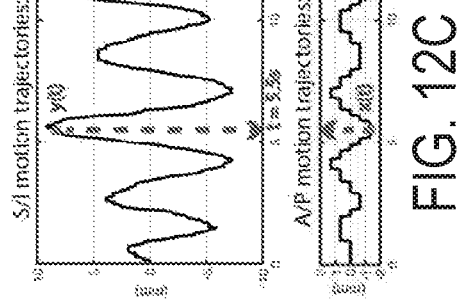
FIG. 12C are graphs showing example motion trajectories, tracked in multiple directions, of targets selected in FIG. 12B, in accordance with aspects of the present disclosure.
Figure 12B:
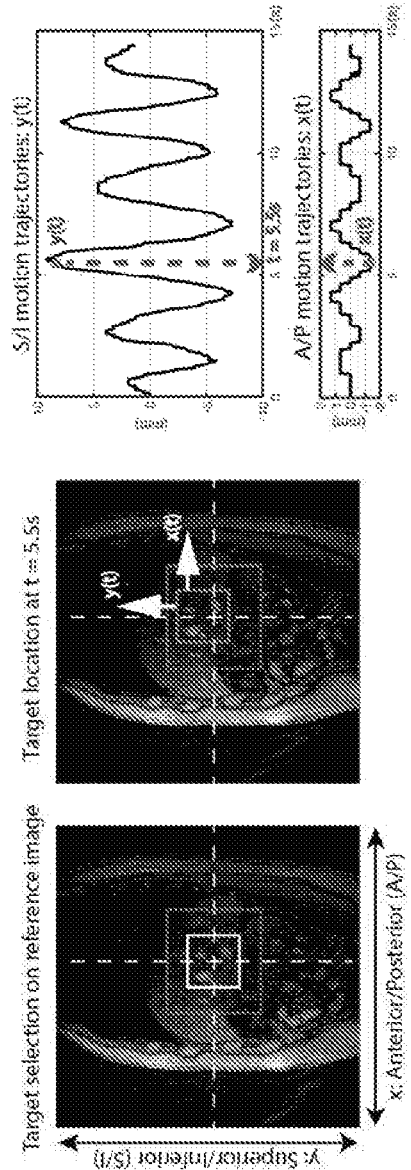
FIG. 12B is another graphical illustration showing target selection and location, in accordance with aspects of the present disclosure.

Image-based Tracking: Images with higher SNR and spatial resolution were reconstructed with a wider temporal footprint (RW1). Specific features of the target tissue were identified (FIG. 12A). A template-matching algorithm was used to track the 2D translational motion of the target features (FIGS. 12B-12C).

Figure 13A:
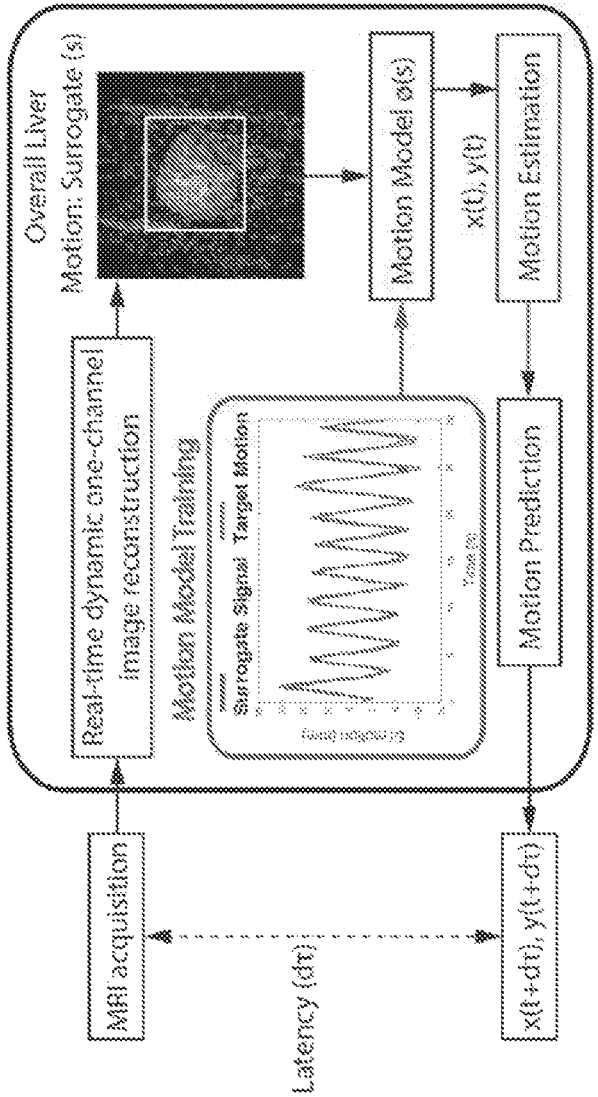
FIG. 13A is yet another graphical illustration showing steps of a process for motion prediction, in accordance with aspects of the present disclosure.
Figure 13B:
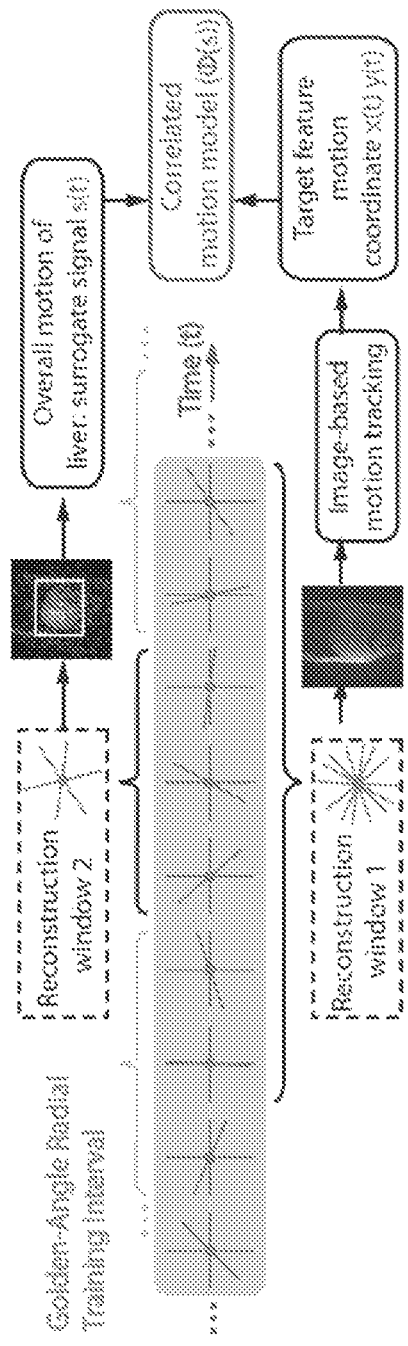
FIG. 13B is yet another graphical illustration showing motion model training, in accordance with aspects of the present disclosure.

Surrogate-based Tracking: Low-resolution images were also reconstructed with narrow temporal footprint (RW2 in FIG. 11B). Overall liver motion was extracted from the images as the surrogate signal to train a motion model for target feature motion estimation (FIG. 13). A quadratic model ($\phi$) was constructed from superior/inferior motion (y) of the target feature and surrogate signal(s):

$$y(t) = \phi(s) = as^2 + bs + c - d\dot{s} + e\dot{s}^2 \qquad \text{Eqn. (8).}$$

Figure 14:
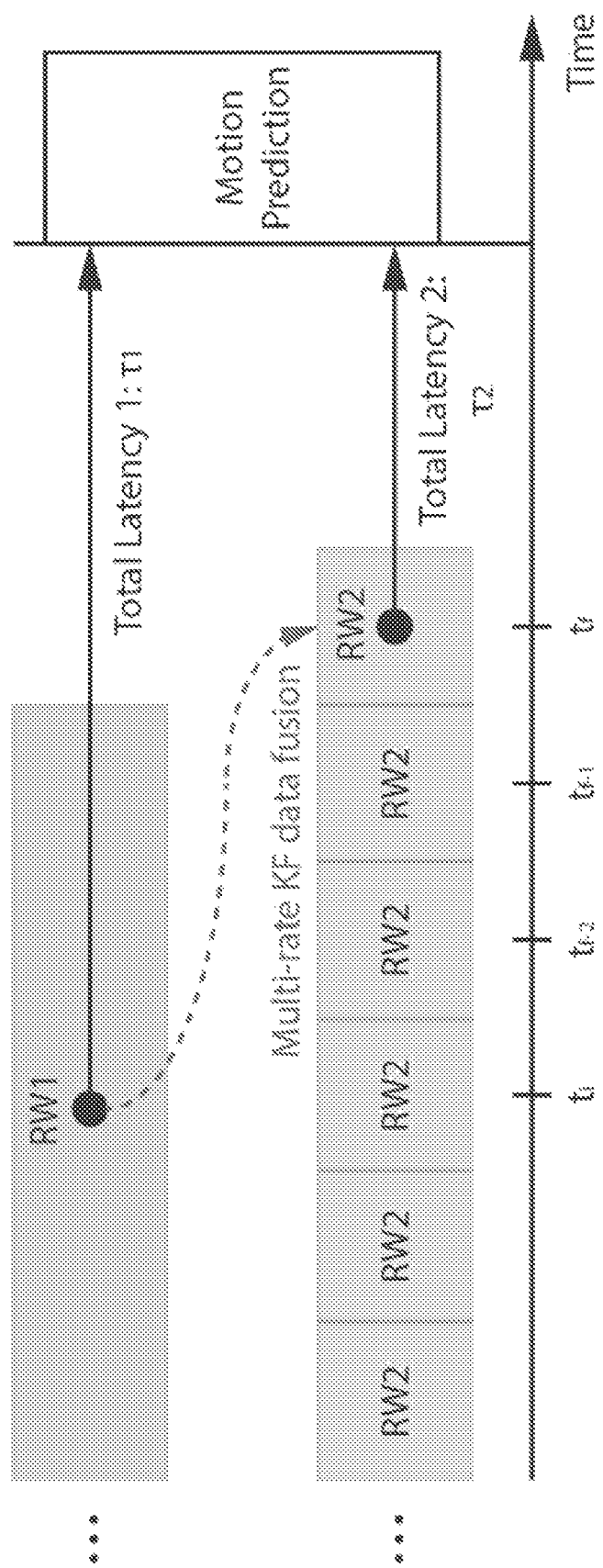
FIG. 14 is yet another graphical illustration showing multi-rate Kalman filter (KF) data fusion, in accordance with aspects of the present disclosure.

Multi-rate Kalman filter (KF): A data fusion framework using KF was established based on the multi-rate characteristics of image-based and surrogate-based tracking (FIG. 14). Surrogate-based tracking was designated as the frequent KF (FKF) agent, which was updated at a higher temporal rate with low latency. Image-based tracking was the infrequent KF (IKF) agent, which was updated at a lower temporal rate with higher latency. Robustness of motion state estimation using the FKF agent was improved by fusing the estimation from the IKF agent, which improves spatial accuracy of motion prediction.

Evaluation: The multi-rate motion prediction framework was implemented offline to simulate real-time processing with GA radial sampling (FIG. 14).

Surrogate-based Tracking: 4 target regions in the liver were selected for image-based tracking and extracted motion coordinates were set as ground truth ($y_g$). A denoising KF was applied to decrease surrogate noise, which is independent of the multi-rate KF, requiring a separate training. Tracking error (TRE) was defined as:

$$TRE(t) = |\phi(s(t)) - y_g(t)| \qquad \text{Eqn. (9).}$$

Mean differences in root-mean-square error (RMSE, mm) of TRE with and without denoising KF were assessed using one-tailed paired-sample t-test (p<0.05 considered significant)

Motion Prediction: The latencies were calibrated (FIG. 14) and prediction results using the proposed multi-rate KF were compared with using only image-based or surrogate-based tracking for 36 target features. The ground truth feature coordinates were extracted at the time point of motion prediction with retrospectively reconstructed high-resolution images. Differences in RMSE and the percentage of prediction error greater than 2.5 mm ($\varepsilon_{2.5}$, %) were compared using non-parametric tests (p<0.05 considered significant). The threshold was selected in a manner similar to the way physicians target lesions with diameter≥5 mm.

Figures 15A, 15B, 15C:
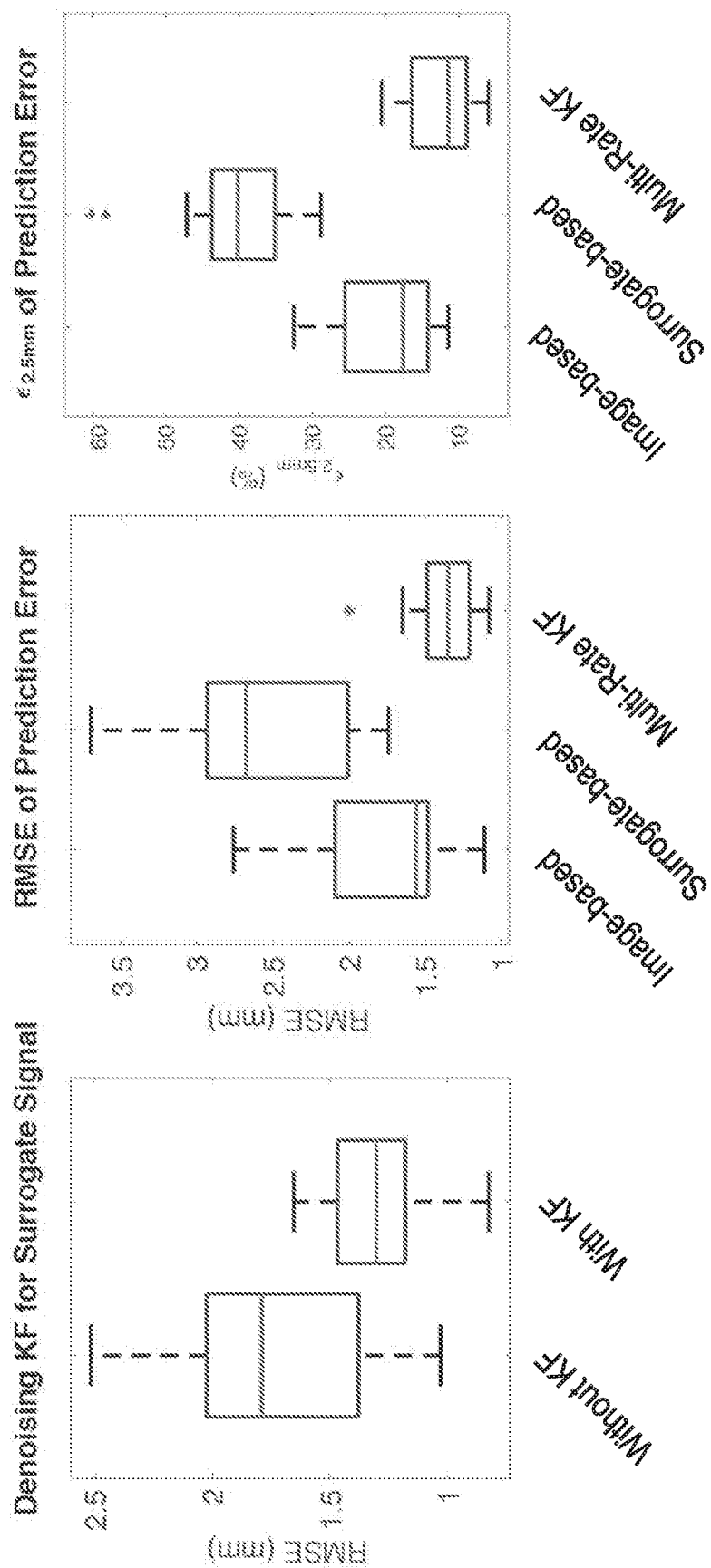
FIG. 15A is a graph showing RMSE of tracking error with and without KF denoising for surrogate-based tracking, in accordance with aspects of the present disclosure.
FIG. 15B is a graph comparing RMSE of prediction error for different motion prediction methods.
FIG. 15C is a graph comparing tolerance of prediction error for different motion prediction methods.

Results of Surrogate-based Tracking: The mean of RMSE of TRE using denoising KF is significantly lower than the results without using denoising KF (1.350 mm versus 1.765 mm, p=0.0062) (FIG. 15A).

Motion Prediction: The mean of both RMSE and c using multi-rate KF motion prediction were significantly lower than that using only surrogate-based or image-based tracking. In addition, the variance of RMSE using multi-rate KF motion prediction was significantly lower than the other methods; there was no significant difference in variance of £2.5 among methods (FIG. 15B-C).

These experimental results provide evidence that the proposed multi-rate motion prediction framework can achieve significantly higher spatial accuracy (RMSE=1.39±0.60 mm) than using only surrogate-based or image-based tracking, and reduce latency compared to image-based tracking. Consistency in motion prediction accuracy was also improved using this multi-rate framework (lower variance in RMSE). Additional model-based processing of surrogate-based tracking has potential to improve the framework. Further work may utilize more datasets and implement online processing.

In one representative demonstration of this invention, a multi-rate motion prediction framework with GA radial acquisition was utilized to combine the advantages of image-based and surrogate-based motion tracking for real-time MM guided interventions. Results herein demonstrate the feasibility of the proposed multi-rate framework in reducing motion prediction error for low-latency feedback.

This present disclosure provides a novel approach that implements a new real-time motion prediction algorithm. As described, systems and methods described may be used for example, in real-time MIll and MM-guided interventions, as well as other procedures. Feasibility for online real-time processing was demonstrated in motion phantom experiments. Simulations and analyses showed that KFEM is a practical method to achieve accurate prediction and MRKF can enhance the accuracy and temporal rate of motion prediction for feedback control.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for predicting motion of a target using imaging, the method comprising:
   receiving image data, acquired using an imaging system, corresponding to a region of interest ("ROI") in a subject;
   generating a set of multi-rate images from the image data, wherein the set of multi-rate images comprises a first set of images and a second set images, wherein a temporal rate of the second set of images is higher than a temporal rate of the first set of images and a spatial resolution of the second set of images is lower than a spatial resolution of the first set of images;
   processing the set of multi-rate images to obtain motion information associated with a target in the ROI, the processing of the set of multi-rate images comprising generating a first motion waveform using the first set of images and a second motion waveform using the second set of images, wherein the second motion waveform is shifted in time relative to the first motion waveform; and utilizing the motion information in a motion prediction framework to estimate a predicted motion of the target; and generating a report based on the predicted motion.

2. The method of claim 1, wherein the image data comprises magnetic resonance imaging ("MRI") data, X-ray data, computed tomography ("CT") data, positron emission tomography ("PET") data, ultrasound ("US") data, or optical image data.

3. The method of claim 1, further comprising using a least squares registration algorithm to generate at least one of the first motion waveform and the second motion waveform.

4. The method of claim 1, further comprising performing a multi-rate adaptive filtering technique using the first motion waveform and the second motion waveform, in combination with supplementary measurements, to estimate a motion state variable.

5. The method of claim 1, further comprising performing a multi-rate adaptive filtering technique, using the first motion waveform and the second motion waveform, to estimate a motion state variable.

6. The method of claim 5, wherein the multi-rate adaptive filtering comprises applying a Kalman filter technique.

7. The method of claim 5, further comprising estimating the predicted motion of the target using at least one of the multi-rate adaptive filtering technique or motion state variable.

8. The method of claim 5, further comprising performing an adaptive calibration to at least one of the multi-rate adaptive filtering technique or motion state variable when a motion prediction error exceeds a threshold.

9. The method of claim 5, wherein the motion state variable is estimated before or during an intervention.

10. The method of claim 1, further comprising providing the report to an interventional system or a graphical user interface.

11. A system for predicting motion of a target using imaging, the system comprising:
an input in communication with an imaging system configured to acquire image data from a subject correspond to a region of interest ("ROI") in a subject;
at least one processor configured to:
receive the image data from the imaging system using the input;
reconstruct a set of images using the image data, wherein the set of images include multi-rate images, and the set of multi-rate images comprises a first set of images and a second set images, wherein a temporal rate of the second set of images is higher than a temporal rate of the first set of images and a spatial resolution of the second set of images is lower than a spatial resolution of the first set of images;
process the set of images to obtain motion information associated with a target selected in the ROI, the processing of the set of images comprising generating a first motion waveform using the first set of images and a second motion waveform using the second set of images, wherein the second motion waveform is shifted in time relative to the first motion waveform;
estimate, using a motion prediction framework, a predicted motion of the target using the motion information; and
generate a report based on the predicted motion; an output for providing the report.

12. The system of claim 11, wherein the input is further configured to obtain supplementary measurements from the subject.

13. The method system of claim 11, wherein the at least one processor is further configured to perform a multi-rate adaptive filtering technique, using the first motion waveform and the second motion waveform, to estimate a motion state variable.

14. The system of claim 13, wherein the at least one processor is further configured to perform an adaptive calibration to at least one of the adaptive filter or motion state variable when a motion prediction error exceeds a threshold.

15. The system of claim 11, wherein the at least one processor is further configured to perform an adaptive filtering technique, using the first motion waveform and the second motion waveform, in combination with supplementary measurements, to estimate a motion state variable.

16. The system of claim 11, wherein the output is in communication with an intervention system, and the report generated is configured to control operation of the interventional system.

* * * * *